(12) United States Patent
Kemler

(10) Patent No.: US 11,877,950 B1
(45) Date of Patent: Jan. 23, 2024

(54) NASAL WARMING FOR VIRAL INFECTION PROTECTION

(71) Applicant: James E. Kemler, Glen Arbor, MI (US)

(72) Inventor: James E. Kemler, Glen Arbor, MI (US)

( * ) Notice: Subject to any disclaimer, the term of this patent is extended or adjusted under 35 U.S.C. 154(b) by 0 days.

(21) Appl. No.: 18/318,671

(22) Filed: May 16, 2023

(51) Int. Cl.
A61F 7/00 (2006.01)

(52) U.S. Cl.
CPC ...... *A61F 7/007* (2013.01); *A61B 2562/0271* (2013.01); *A61F 2007/0006* (2013.01)

(58) Field of Classification Search
CPC ............. A61F 7/007; A61F 2007/0006; A61B 2562/0271
See application file for complete search history.

(56) References Cited

U.S. PATENT DOCUMENTS

| | | | |
|---|---|---|---|
| 4,401,114 A | 8/1983 | Woff et al. | |
| 5,697,100 A | 12/1997 | Horowitz et al. | |
| 6,244,265 B1 | 6/2001 | Cronk et al. | |
| 11,364,143 B2 | 6/2022 | Draper | |
| 2008/0178874 A1 | 7/2008 | Doshi et al. | |
| 2009/0062733 A1 | 3/2009 | Shannon | |
| 2015/0209174 A1* | 7/2015 | Abreu ....................... | A61F 7/02 607/104 |
| 2021/0068483 A1 | 3/2021 | Dimsey | |

FOREIGN PATENT DOCUMENTS

| | | |
|---|---|---|
| CN | 113827395 A | 12/2021 |
| JP | 2007098092 A | 4/2007 |
| KR | 102068786 B1 | 1/2020 |

OTHER PUBLICATIONS

Eccles, Ronald article titled "The role of nasal congestion as a defence against respiratory viruses," © 2020 John Wiley & Sons Ltd, wileyonlinelibrary.com/journal/coa, Clinical Otolaryngology. 2021;46:4-8., Accepted: Oct. 10, 2020, DOI: 10.1111/coa.13658.
Frieden, Joyce article titled "Masking Yields Small Reduction in COVID Risk, Review Concludes—Surgical masks or N95s should still be worn in healthcare settings, urge editorial authors," Washington Editor, MedPage Today dated May 15, 2023 (8 pages).

(Continued)

*Primary Examiner* — Joseph A Stoklosa
*Assistant Examiner* — Adam J Avigan
(74) *Attorney, Agent, or Firm* — Aurora Consulting LLC; Kristen J. Hansen; Ashley Sloat

(57) ABSTRACT

Systems and methods are described for devices that may include a nasal assembly comprising: a first support member having a first surface configured to substantially conform to a sinistral contour of a nose when the nasal assembly is being worn; a second support member having a second surface configured to follow a dextral contour of the nose when the nasal assembly is being worn; and a heat source electrically coupled to the first support member and the second support member, the heat source being configured to adjust a surface temperature of the first surface and the second surface to cause warming of the sinistral contour of the nose and the dextral contour of the nose to a predefined temperature range.

26 Claims, 13 Drawing Sheets

(56) References Cited

OTHER PUBLICATIONS

Hayes, Bradley T. et al. article titled "Three-MHz Ultrasound Heats Deeper Into the Tissues Than Originally Theorized," Journal of Athletic Training 2004;39(3):230-234, by the National Athletic Trainers' Association, Inc., www.journalofathletictraining.org, vol. 39, No. 3, Sep. 2004.

Huang, PhD, Di et al. article titled "Cold exposure impairs extracellular vesicle swarm-mediated nasal antiviral immunity," J Allergy Clin Immunol, vol. 151, No. 2, Feb. 2023.

Mourtzoukou et al. article titled "Exposure to cold and respiratory tract infections," Int J Tuberc Lung Dis 11(9):938-943 @ 2007 The Union, article submitted Feb. 23, 2007, Final version accepted May 1, 2007 (6 pages).

\* cited by examiner

NASAL WARMING FOR VIRAL INFECTION PROTECTION

INCORPORATION BY REFERENCE

All publications and patent applications mentioned in this specification are herein incorporated by reference in their entirety, as if each individual publication or patent application was specifically and individually indicated to be incorporated by reference in its entirety.

TECHNICAL FIELD

This disclosure relates generally to the field of warming devices, and more specifically to the field of warming devices having nasal mucosa heating features.

BACKGROUND

The term "nasal cavity" may refer to an internal portion of the nose that includes each of a sinistral and a dextral side of the nose. The nasal cavity functions to condition the air entering the nasal vestibule of the nose for preparation to be received by the other areas of the respiratory tract. The nasal cavity may include a number of extracellular vesicles (EVs) that function to provide cell-to-cell communication within the tissues of the nasal cavity. EVs may transport content such as DNA, RNA, proteins, and small molecules from cell to cell.

SUMMARY

There is a need for new and useful systems and methods for boosting an ability of the nasal cavity to fend off viral and/or bacterial particles.

In some aspects, the techniques described herein relate to a nasal assembly including: a first support member having a first surface configured to substantially conform to a sinistral contour of a nose when the nasal assembly is being worn; a second support member having a second surface configured to follow a dextral contour of the nose when the nasal assembly is being worn; and a heat source electrically coupled to the first support member and the second support member, the heat source being configured to adjust a surface temperature of the first surface and the second surface to cause warming of the sinistral contour of the nose and the dextral contour of the nose to a predefined temperature range.

In some aspects, the techniques described herein relate to a nasal assembly, wherein: the sinistral contour of the nose is within a first portion of a nasal cavity of the nose and the dextral contour of the nose is within a second portion of the nasal cavity; and the first surface and the second surface are configured to cause respective warming of the first portion of the nasal cavity and the second portion of the nasal cavity to the predefined temperature range when the first surface and the second surface are heated, the predefined temperature range being between about 37 degrees Celsius and about 39 degrees Celsius.

In some aspects, the techniques described herein relate to a nasal assembly, wherein: the first portion of the nasal cavity includes a sinistral nostril having a first tissue portion lined with a first mucous layer; the second portion of the nasal cavity includes a dextral nostril having a second tissue portion lined with a second mucous layer; and wherein the first surface and the second surface are configured to cause respective warming of the first tissue portion and the second tissue portion when the first surface is placed in contact with the sinistral contour and the second surface is placed in contract with the dextral contour.

In some aspects, the techniques described herein relate to a nasal assembly, wherein the nasal assembly further includes: a sensor adapted to be in contact with at least a portion of a nasal cavity of the nose, the sensor being configured to monitor a portion of the nasal cavity; and a power source mounted on the first support member or the second support member, the power source being electrically coupled to the heat source and the sensor.

In some aspects, the techniques described herein relate to a nasal assembly, wherein the sensor is a temperature sensor configured to: monitor a temperature of the portion of the nasal cavity; in response to detecting that a surface temperature of the portion of the nasal cavity is below the predefined temperature range, causing the heat source to activate to perform a heating cycle; and in response to detecting that the surface temperature of the portion of the nasal cavity is above the predefined temperature, causing deactivation of the heat source.

In some aspects, the techniques described herein relate to a nasal assembly, wherein the sensor is a temperature sensor configured to: monitor a temperature of an environment surrounding the nasal assembly; and transmit a signal to the heat source to selectively activate the heat source based on the temperature of the environment surrounding the nasal assembly.

In some aspects, the techniques described herein relate to a nasal assembly, wherein the nasal assembly further includes: an antenna circuit configured to communicate wirelessly with at least one external computing device to enable the at least one external computing device to wirelessly operate the nasal assembly.

In some aspects, the techniques described herein relate to a nasal assembly, wherein the first support member is an intranasal insert configured to warm a nasal cavity of the nose, the intranasal insert including: an elongated body having a length sufficient to extend through a nasal vestibule of the nose and into at least a portion of the nasal cavity when the elongated body is inserted into a nostril of the nose, wherein the elongated body includes an exterior surface having a plurality of nonstationary baffles configured to increase resistance to airflow within the nostril.

In some aspects, the techniques described herein relate to a nasal assembly, wherein the plurality of nonstationary baffles includes flexible flaps, slits, cutouts, or perforations that allow air to flow from an interior surface of the elongated body to the exterior surface of the elongated body. In some aspects, the techniques described herein relate to a nasal assembly, wherein the intranasal insert is an additively manufactured, continuous lattice structure configured to generate a pressure on a surface of a portion of the nasal cavity when inserted into the nostril to cause a partial constriction of the nostril.

In some aspects, the techniques described herein relate to a nasal assembly, wherein: the sinistral contour of the nose and the dextral contour of the nose are external anatomical regions of the nose; and the first surface and the second surface are configured to cause warming of one or more internal portions of the nose to the predefined temperature range when the first surface and the second surface are heated, the predefined temperature range being about 41 degrees Celsius to about 43 degrees Celsius, wherein the one or more internal portions of the nose are opposite the external anatomical regions of the nose at respective locations of the sinistral contour and the dextral contour of the nose.

In some aspects, the techniques described herein relate to a nasal assembly, wherein: the external anatomical regions of the nose include a surface of at least one of: a bridge, a sinistral nasal sidewall, a dextral nasal sidewall, an accessory nasal cartilage, or a septal cartilage; and heating the first surface and the second surface causes warming of the one or more internal portions of the nose to the predefined temperature range, the one or more internal portions of the nose being opposite the respective bridge, the sinistral nasal sidewall, the dextral nasal sidewall, the accessory nasal cartilage, or the septal cartilage. In some aspects, the techniques described herein relate to a nasal assembly, wherein the predefined temperature range is about 37 degrees Celsius to about 39 degrees Celsius.

In some aspects, the techniques described herein relate to a nasal assembly, wherein the first support member is coupled to the second support member by a bridge member having a substantially C-shaped structure.

In some aspects, the techniques described herein relate to a nasal assembly, wherein the bridge member includes: a first end coupled to the first support member; a second end coupled to the second support member, the bridge member being configured to: cause the first support member to exert pressure on the sinistral contour of the nose; and cause the second support member to exert pressure on the dextral contour of the nose.

In some aspects, the techniques described herein relate to a nasal assembly, wherein exerting pressure on the sinistral contour of the nose causes a sinistral wall of the nose to move inward toward a central axis of the nose to narrow a sinistral nostril of the nose and exerting pressure on the dextral contour of the nose causes a dextral wall of the nose to move inward toward the central axis of the nose to narrow a dextral nostril of the nose. In some aspects, the techniques described herein relate to a nasal assembly, wherein the nasal assembly is configured to removably attach to a bridge portion of eyeglasses or a lens of the eyeglasses.

In some aspects, the techniques described herein relate to a wearable system for warming a nasal cavity, the system including: a processor; a sensor adapted to be placed adjacent to a portion of a nose and configured to sense a temperature of the portion of the nose and wirelessly output the sensed temperature to the processor; and a heat source communicatively coupled to the sensor and the processor, the heat source being placed in contact with a contour of the nose, wherein the processor is configured to receive the sensed temperature of the nose and cause the heat source to modify a temperature of the nasal cavity based on the sensed temperature of the nose.

In some aspects, the techniques described herein relate to a system, wherein: the portion of the nose is a portion of the nasal cavity; and the sensor is installed in an item of jewelry configured to be placed in a nose piercing associated with the nose such that the sensor is in contact with the portion of the nasal cavity when the item of jewelry is worn in the nose piercing, the sensor being further configured to monitor an internal temperature of the nasal cavity and wirelessly communicate with the processor and the heat source to trigger warming of the nasal cavity until a target temperature range is achieved. In some aspects, the techniques described herein relate to a system, wherein the target temperature range is about 37 degrees Celsius to about 39 degrees Celsius.

In some aspects, the techniques described herein relate to a system, wherein: the heat source is an item of jewelry configured to be placed in a nose piercing associated with the nose such that the heat source is in contact with a portion of a nasal cavity associated with the nose when the item of jewelry is worn in the nose piercing; the sensor is installed within a bridge member configured to be worn on the nose; and the heat source is further configured to warm an interior surface of the nose in response to the sensor detecting the temperature of the nose is outside of a target temperature range.

In some aspects, the techniques described herein relate to a system, wherein the sensor is adapted to be worn within a portion of the nasal cavity. In some aspects, the techniques described herein relate to a system, further including one or more antennas configured to wirelessly communicate with a mobile computing device to selectively activate the heat source based on a detected temperature of an environment surrounding the wearable system.

In some aspects, the techniques described herein relate to a method for reducing virus replication in a nasal mucosa, the method including: providing a device in contact with a contour of a nose of a user, the device including a warming assembly and a temperature sensor, wherein the device is configured to at least partially constrict airflow into the nose; monitoring, by the temperature sensor, a temperature of portion of the nose; and in response to detecting, by the temperature sensor and for the portion of the nose, that the temperature is below a predefined temperature range, causing activation of the warming assembly to increase the temperature of the portion of the nose to be within a predefined temperature range; and maintaining the temperature of the portion of the nose within the predefined temperature range until receiving a signal to cause deactivation of the warming assembly.

In some aspects, the techniques described herein relate to a method, wherein the portion of the nose is an inferior turbinate and the predefined temperature range is about 37 degrees Celsius to about 39 degrees Celsius. In some aspects, the techniques described herein relate to a method, wherein the portion of the nose is a nasal vestibule and the predefined temperature range is about 41 degrees Celsius to about 43 degrees Celsius. In some aspects, the techniques described herein relate to a method, further including: deactivating the warming assembly when the portion of the nose reaches a temperature within the predefined temperature range.

In some aspects, the techniques described herein relate to a method, wherein the device further includes an antenna circuit configured to communicate wirelessly with at least one external computing device to enable the at least one external computing device to wirelessly operate the device, the method further including: monitoring a temperature of an environment surrounding a portion of the device; and sending a signal to the warming assembly to selectively activate the warming assembly based on the temperature of the environment surrounding the portion of the device.

In some aspects, the techniques described herein relate to a method, wherein at least partially constricting airflow into the nose includes at least partially obstructing a nostril of the nose. In some aspects, the techniques described herein relate to a method, wherein the device includes a convex midsection located centrally between a first end portion and a second end portion of the device, the midsection being adapted to form to the contour of the nose.

The details of one or more implementations are set forth in the accompanying drawings and the description below.

Other features will be apparent from the description and drawings, and from the claims.

BRIEF DESCRIPTION OF THE DRAWINGS

The foregoing is a summary, and thus, necessarily limited in detail. The above-mentioned aspects, as well as other aspects, features, and advantages of the present technology are described below in connection with various embodiments, with reference made to the accompanying drawings.

Figure 1:
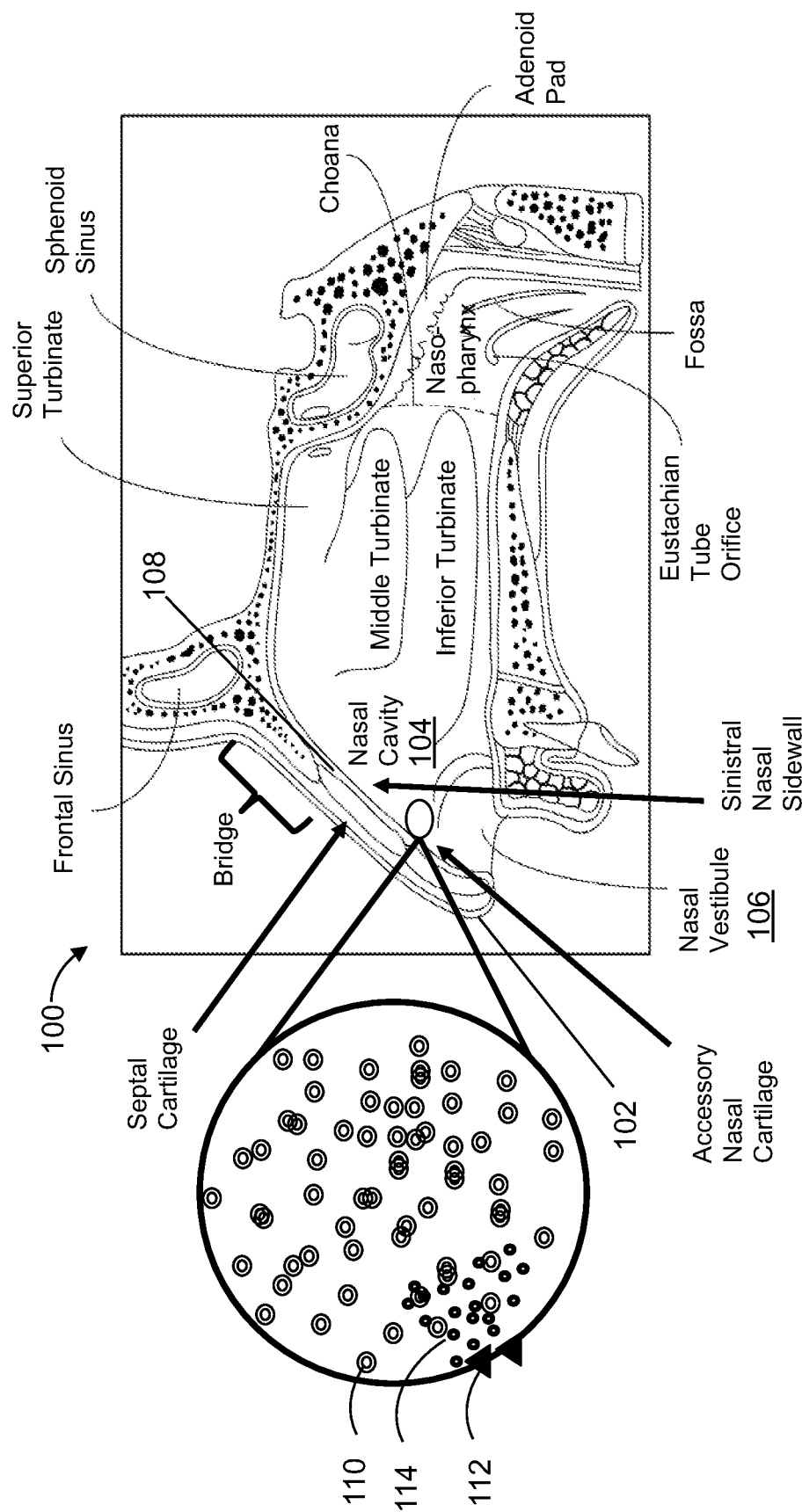
FIG. 1 illustrates an example diagram of human nasal anatomy.

The illustrated embodiments are merely examples and are not intended to limit the disclosure. The schematics are drawn to illustrate features and concepts and are not necessarily drawn to scale.

DETAILED DESCRIPTION

The foregoing is a summary, and thus, necessarily limited in detail. The above-mentioned aspects, as well as other aspects, features, and advantages of the present technology will now be described in connection with various embodiments. The inclusion of the following embodiments is not intended to limit the disclosure to these embodiments, but rather to enable any person skilled in the art to make and use the claimed subject matter. Other embodiments may be utilized, and modifications may be made without departing from the spirit or scope of the subject matter presented herein. Aspects of the disclosure, as described and illustrated herein, can be arranged, combined, modified, and designed in a variety of different formulations, all of which are explicitly contemplated and form part of this disclosure.

Recent history has shown that many conventional strategies including at least viral reducing products, viral reducing medications, and ill-fitting or low quality masks have proven suboptimal in reducing infection and/or viral replication in the human population. For example, viruses such as the common cold or SARS-CoV-2 have not been affected by conventional virus blocking strategies. In general, the common cold or SARS-CoV-2 can begin replicating at an increased rate at temperatures below about 37 degrees Celsius because these virus cells replicate more efficiently at lower temperatures. Applying conventional virus blocking strategies does nothing to exploit the weaknesses of viruses that have an inability to replicate (or are slower to replicate) at temperatures above about 37 degrees Celsius. The systems and methods described herein may solve this technical problem pertaining to viral replication in the nasal mucosa and the nasal cavity, in general. For example, the systems and methods described herein may reduce the risk of viral infection and/or further viral replication by increasing a temperature of the nasal cavity and/or nasal mucosa of the nose.

Because colder temperatures in the interior of the nose can significantly decrease the ability of the body to prevent viral infection (through a mechanism of reduced extracellular vesicle (EV) generation). The systems and methods described herein provide a way to warm the nasal cavity, maintain a particular temperature of the nasal cavity, and/or increase EV generation in the nasal cavity by providing a nasal assembly that produces heat in or on portions of the nose.

The systems and methods described herein provide an advantage of offering a minimally obtrusive approach, in comparison to masks and other options which obscure the face. The direct heating and/or compression of portions of the nose provided by the systems and methods described herein allow for an efficient and effective method to heat the interior of the nose than conventional systems and/or medications.

In particular, disclosed herein are systems and methods for warming all or a portion of a nasal cavity in a nose of a user. For example, internal and external wearable devices for warming the nasal cavity are described in detail throughout this disclosure. These internal devices, external devices, or combination internal/external devices may function alone or in combination to reduce viral (and/or bacterial) cell replication in the nasal cavity. The devices may reduce viral cell replication (and/or bacterial cell replication) in the nasal cavity by maximizing heat transfer to the nasal cavity. For example, the devices, systems, and methods described herein function to heat (e.g., warm, increase temperature, etc.) the nasal cavity to reduce a likelihood that viral particles (and/or bacterial particles) will reproduce in nasal mucosa within the nasal cavity.

Reducing the likelihood of replication of virus cells in the nasal mucosa may provide an advantage of reducing or blocking the virus from infecting cells in the nasal mucosa and/or nasal cavity, and thus reducing or blocking the viral infection of the nose and body of the user. In addition, the devices described herein may reduce the likelihood of replication of viral particles without the use of masks (e.g., nose/mouth coverings). In some implementations, the devices described herein may be incorporated into wearable objects for convenience in wearing the devices. The wearable objects may include, but are not limited to, eyeglasses, jewelry, nose plugs, nose clips, lens attachment, and any combination thereof.

FIG. 1 illustrates an example diagram of human nasal anatomy 100. The anatomy 100 includes a nose 102, a nasal cavity 104, and portions of the sinuses and adenoids. The nasal vestibule 106 is shown as an entrance to the nose 102. The nasal vestibule 106 may receive air and particulate that may be passed through nasal mucosa 108 to the nasal cavity 104. The nasal cavity 104 may include any number of nasal cells 110. The nasal cells may release (e.g., generate and emit) extracellular vesicle (EV) particles 114 to protect the cells 110 from viral infection.

Extracellular vesicle (EV) particles 114 may include a number of proteins (not shown) that are typically found on a surface of a nasal cell 110. The proteins on the EV particles 114 may function to attract the virus particles 112 to the EV particles 114 to prevent virus particles 112, for example, from infecting the cells 110 with the virus. By releasing EV particles 114 to attach to, and thus neutralize the virus particles 112, the nasal cavity 104 may protect against viral infection when the nasal cavity 104 can be maintained at a predefined temperature (i.e., at or above normal human body temperature of about 36 degrees Celsius to about 37 degrees Celsius). However, when the temperature of the nasal cavity 104 drops below about 36 degrees Celsius, the generation and release of the EV particles 114 may not function efficiently in that fewer EV particles 114 are generated and/or released at temperatures below normal human body temperature. This can increase the likelihood that a virus particle 112 or a bacterial particle will infect a nasal cell 110.

In general, the nasal cavity 104 may filter and humidify the air when the air passes into the nose 102. The filtering may be performed by vibrissae (not shown) and/or cilia (not shown) within the vestibule 106 by accumulating particulate matter. For example, the nasal mucosa 108 of the nasal cavity 104 includes layers of tissue lined by a layer of mucus (not shown) and vibrissae (not shown) and cilia (not shown), each of which is positioned along a surface of the nasal cavity 104. The mucus may cause adherence of particulate to the nasal mucosa 108 and/or the vibrissae and/or the cilia, any or all of which may collect or remove (e.g., catch) the particulate from the inhaled air. While the nasal cavity 104 and associated anatomical structures in the nasal cavity may provide a partial filtering effect by cleaning and purifying air that is introduced to the body, the nasal cavity 104 alone is not aptly configured to provide a strong defense against bacterial and viral invaders.

For example, as the nasal cavity 104 warms and filters the inhaled air, the nasal mucosa 108 (and/or the nasal cavity itself) may cool to a temperature below a normal human body temperature (i.e., about 37 degrees Celsius). Unobstructed air flow into the nasal cavity in periods of external cold temperature has been demonstrated in studies to cool the internal nasal temperatures to a significant degree. For example, a study by Huang, et. al. [*Cold exposure impairs extracellular vesicle swarm-mediated nasal antiviral immunity,*" February 2023] at p. 521, indicates that "the intranasal temperature at the level of anterior and midinferior turbinate dropped 6.4° C. (P<_0.001) and 4.7° C. (P<_0.001) maximum, respectively, after a reduction in ambient temperature from 23.3° C. to 4.4° C." When the temperature of the nasal mucosa 108 and/or the nasal cavity 104 drop below such temperatures, the nasal cavity 104 may become susceptible to particular viruses and/or bacteria. For example, viruses such as the common cold or SARS-CoV-2 can begin replicating at an increased rate at temperatures below about 37 degrees Celsius because these virus cells replicate more efficiently at lower temperatures, and the EV particles are reduced, with statistical significance [Id. at p. 513, section 3] by relatively small drops in internal nasal temperature (as low as 5 degree C.) as well. Conversely, when a temperature of the nasal mucosa 108 (or the nasal cavity 104) is increased to and/or maintained at about 37 degrees Celsius or higher, virus replication becomes less efficient and EV particles 114 activate to ward off viral particle infection/replication within nasal cells 110.

Accordingly, the devices described herein may prevent or reduce the likelihood of viral particle replication within a nasal cell 110 by increasing or maintaining a temperature within the nasal cavity 104. For example, the devices described herein may include a heating source to increase or maintain a temperature of the nasal cavity 104 and/or an environment around the nasal cavity 104. The heating source may cause warming of portions of the nose 102 to maintain, for at least a portion of the vestibule 106 and/or nasal cavity 104, a temperature of about 37 degrees Celsius to about 39 degrees Celsius. The devices described herein may be configured to apply warmth externally or internally to reduce virus replication in nasal mucosa of a nose of a user. For example, the devices described herein may apply heat to external portions of the nose 102 and/or internal portions of the nose 102. Such devices may trigger heating cycles that increase a temperature within the vestibule 106 and/or within the nasal cavity 104 to cause EV particle 114 generation to stop or reduce viral replication within the nasal cavity 104, nasal mucosa 108, and/or surrounding tissues.

Systems and Devices

FIGS. 2A-2E illustrate example embodiments of nasal assemblies for warming a portion of the nose 102. The embodiments of FIGS. 2A-2E may be configured to be worn external to the nasal cavity 104. For example, each embodiment described in FIGS. 2A-2E may be placed on or near to one or more external contours of the nose 102. As used herein, the phrase "external nasal contours" may include all or a portion of a bridge of the nose, a dorsum nasi of the nose, an apex of the nose, a supra-alar crease of the nose, an ala of the nose, a dextral nasal sidewall, a sinistral nasal sidewall, an accessory nasal cartilage, or a septal cartilage. While the embodiments of FIGS. 2A-2E are described as being wearable external to the nasal cavity 104, the embodiments may function with other devices internal to the nasal cavity 104, and/or computing devices external to the nasal cavity 104. In some implementations, the embodiments of FIGS. 2A-2E may be adapted to function as devices internal to the nasal cavity 104.

Figure 2A:
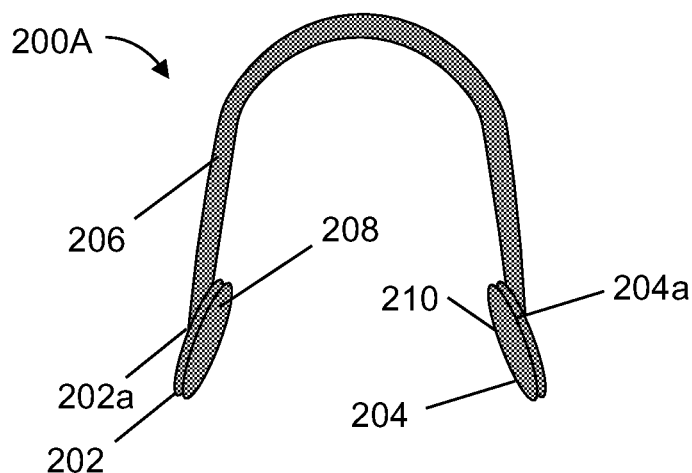
FIGS. 2A-2E illustrate example embodiments of nasal assemblies for warming a portion of the nose.

FIG. 2A illustrates a perspective view of an example nasal assembly 200A for warming at least a portion of the nasal cavity 104. The nasal assembly 200A may be a nose clip or nose adornment that may be removably coupled to be worn on the nose 102 of a user. The nasal assembly 200A includes a first support member 202 and a second support member 204. In some implementations, the first support member 202 is coupled to the second support member 204 by a bridge member 206. The bridge member 206 may be a convex component located at a midsection or intermediate section of the nasal assembly 200A where the midsection is substantially centrally positioned between the first end portion 202*a* and a second end portion 204*a* of the device. The midsection may be adapted to conform to at least a portion of the contour of the nose 102. For example, the midsection may be the entire bridge member 206, which may fit over or on the bridge of the nose. Portions of the bridge member 206 may touch the nose while other portions of the bridge member 206 may be arranged to extend over and above the skin of the bridge of the nose.

In some implementations, the first support member 202 and the second support member 204 are removably attached to the nose 102 of the user without the bridge member 206. For example, support members 202, 204 may be removably attached to the nose 102 by adhesion via glue, sebum, tape, film, or other mechanically adhesive material that may be removed without harm to a skin surface of the nose 102. In some implementations, the support members 202, 204 may be adapted to pinch portions of the nose by clipping onto the nose via a force induced by the bridge member 206. The pinching may cause an exerted pressure on the sinistral contour (e.g., sinistral contour 248 of FIG. 2D) of the nose, which may cause a sinistral wall (e.g., internal to the nose) to move inward toward a central axis (C) of the nose to narrow a sinistral nostril (e.g., nostril 254 of FIG. 2D). In addition, the pinching may simultaneously cause an exerted pressure on the dextral contour (e.g., dextral contour 252 of FIG. 2D) of the nose, which may cause a dextral wall (e.g., internal to the nose) to move inward toward the central axis (C) of the nose to narrow a dextral nostril (nostril 256 of FIG. 2D). For example, the bridge member 206 may include or be formed of a shape memory material such that bridge member 206 can be expanded to be applied to a nose, but then flexes back to its unexpanded state, thereby applying the force to the nose.

The first support member 202 can include a first surface 208 that is configured to substantially conform to a sinistral contour (e.g., sinistral contour 248 of FIG. 2D) of the nose 102 when the nasal assembly 200A is being worn by a user, for example. Similarly, the second support member 204 can include a second surface 210 that is configured to follow a dextral contour (e.g., dextral contour 252 of FIG. 2D) of the nose 102 when the nasal assembly 200A is being worn by a user. In general, the sinistral contour of the nose and the dextral contour of the nose are external anatomical regions of the nose 102, as shown in FIG. 2D. In some implementations, the sinistral contour of the nose and the dextral contour of the nose may be internal contours within the nasal cavity or nose, as shown in FIG. 2D and FIG. 5E, for example.

As shown, the support members 202, 204 are substantially oval in shape. The oval-shaped support members 202, 204 may be arranged along the contours of the nose to cover a portion of a surface area of the nose. While support members 202, 204 are depicted as oval-shaped, one skilled in the art can contemplate substituting a different polygonal shape. The size of the portion of surface area may vary, as described throughout this disclosure. In addition, the support members 202, 204 may cover different portions of the surface area of the nose depending on how the support members 202, 204 are arranged on the nose contours. For example, a user can arrange the assembly 200A transversely along the contours of the nose and/or laterally along the contours of the nose to adjust for comfort. In some implementations, the user can arrange the assembly 200A transversely along the contours of the nose and/or laterally along the contours of the nose to adjust for heating or cooling particular portions of the nose to particular temperatures. In some implementations, heating or cooling the particular portions of the nose may be performed to reduce virus replication in nasal mucosa of a nose of a user.

Figure 8:
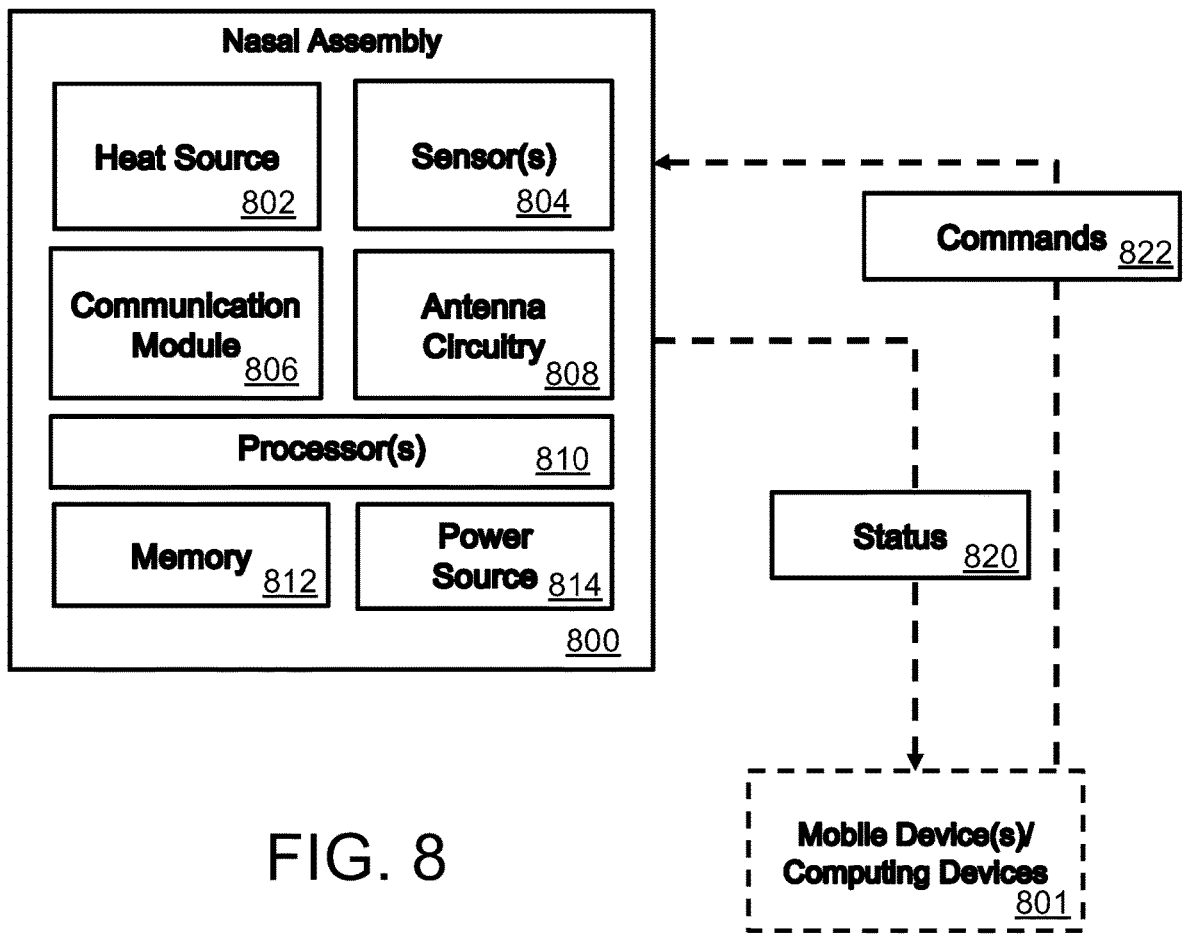
FIG. 8 is an example system for warming and monitoring a portion of the nose.

The nasal assembly 200A may further include a heat source (e.g., heat source 802 of FIG. 8) electrically coupled to the first support member 202 and/or the second support member 204. Although nasal assembly 200A is described as heating both a sinistral and dextral side of a nose, one of skill in the art will appreciate that nasal assembly 200A can also heat a sinistral side and not a dextral side or heat a dextral side and not a sinistral side. The heat source may be a wire, a coil, or other heating element arranged within the support members 202, 204. The heat source may be electrically coupled to electronics and a power source of the nasal assembly 200A to heat or cool the surface of the nose. For example, the heat source may be powered and wired (as shown in FIG. 8) to adjust a surface temperature of the first surface 208 (of the assembly 200A) and/or the second surface 210 (of the assembly 200A) to cause warming of the sinistral contour (e.g., sinistral contour 248 in FIG. 2D) of the nose 102 and the dextral contour (e.g., dextral contour 252 in FIG. 2D) of the nose 102 and further cause warming of one or more internal portions of the nose 102 to the predefined temperature or temperature range. One or more of the internal regions of the nose may be located opposite the external anatomical regions of the nose being heated, which may be at respective locations of the sinistral contour 248 and the dextral contour 252. For example, the external anatomical regions of the nose may include a surface of at least one of: a bridge, a sinistral nasal sidewall, a dextral nasal sidewall, an accessory nasal cartilage, or a septal cartilage, as shown in FIG. 1. In general, heating the first surface 208 and/or the second surface 210 causes warming of one or more internal portions of the nose to a predefined temperature range. The one or more internal portions of the nose 102, for example, may be located opposite the respective external anatomical regions of the bridge, the sinistral nasal sidewall, the dextral nasal sidewall, the accessory nasal cartilage, or the septal cartilage.

An adjustment of the temperature of the surfaces 208, 210 of the respective support members 202, 204 may be performed until a predefined temperature range is achieved. The predefined temperature range may be about 39 degrees Celsius to about 44 degrees Celsius; about 39 degrees Celsius to about 41 degrees Celsius; about 40 degrees Celsius to about 43 degrees Celsius; or about 41 degrees Celsius to about 43 degrees Celsius. In some implementations, the predefined temperature range may be selected to ensure that an interior portion of the nose reaches a particular temperature. For example, the predefined temperature range in which to heat an external surface of the nose may be selected at a range that ensures the inferior turbinate of a nasal cavity of the user wearing nasal assembly 200A, for example, reaches a temperature range of about 37 degrees Celsius to about 39 degrees Celsius. In another example, the predefined temperature range in which to heat an external surface of the nose may be selected at a range that ensures the nasal vestibule reaches a temperature range between about 41 degrees Celsius to about 43 degrees Celsius.

In some implementations, the nasal assembly 200A includes an antenna circuit configured to communicate wirelessly with at least one external computing device to enable the computing device to wirelessly operate the nasal assembly 200A, as described in detail in FIG. 8. In addition, the nasal assembly 200A may include one or more sensors, power sources, and/or processors, as described in detail in FIG. 8. For example, the nasal assembly 200A may include one or more sensors adapted to be placed adjacent to a portion of the nose 102. The one or more sensors may sense a temperature of a portion of the nose 102 and wirelessly output the sensed temperature to the processor.

Figure 2B:
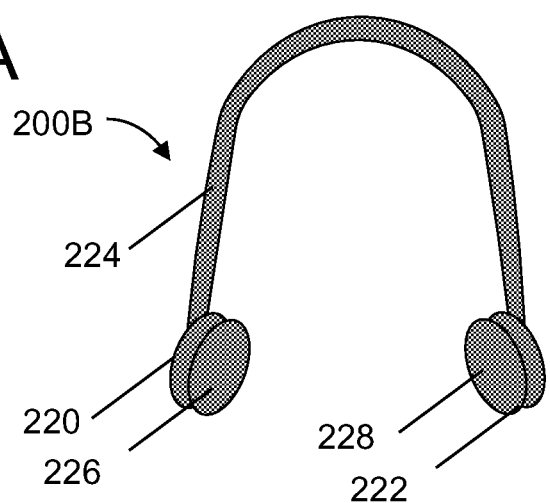

FIG. 2B illustrates a perspective view of another example nose assembly 200B for warming at least a portion of the nasal cavity 104. The nasal assembly 200B may be a nose clip or nose adornment that may be removably coupled to be worn on the nose 102 of a user. The nasal assembly 200A includes a first support member 220 and a second support member 222. In some implementations, the first support member 220 is coupled to the second support member 222 by a bridge member 224. The bridge member 224 may be a convex component located at a midsection or intermediate section of the nasal assembly 200B. The midsection may be adapted to conform to at least a portion of the contour of the nose 102. For example, the midsection may be the entire bridge member 224, which may fit over or on the bridge of the nose. Portions of the bridge member 224 may touch the nose while other portions of the bridge member 224 may be arranged to extend over and above the skin of the bridge of the nose.

In some implementations, the bridge member 224 may have a substantially C-shaped structure. In some implementations, the bridge member 224 may have a substantially flexible structure. In some implementations, the bridge member may also provide warming to one or more portions of the nose 102.

In some implementations, the first support member 220 and the second support member 222 are removably attached to the nose 102 of the user without the bridge member 224. For example, support members 220, 222 may be removably attached to the nose 102 by adhesion via glue, sebum, tape, film, or other mechanically adhesive material that may be removed without harm to a skin surface of the nose 102. In some implementations, the support members 220, 222 may be adapted to pinch portions of the nose by clipping onto the nose via a force induced by the bridge member 224.

The first support member 220 includes a first surface 226 that is configured to substantially conform to a sinistral contour (e.g., sinistral contour 248 of FIG. 2D) of the nose 102 when the nasal assembly 200B is being worn by a user, for example. Similarly, the second support member 222 includes a second surface 228 that is configured to follow a dextral contour (e.g., dextral contour 252 of FIG. 2D) of the nose 102 when the nasal assembly 200B is being worn by a user, for example.

The support members 220, 222 can be substantially circular in shape. The circular-shaped support members 220, 222 may be arranged along the contours of the nose to cover a portion of a surface area of the nose. While support members 220, 222 are depicted as circular-shaped, one skilled in the art can contemplate substituting a different polygonal shape. The size of the portion of surface area may vary, as described throughout this disclosure. In addition, the support members 220, 222 may cover different portions of the surface area of the nose depending on how the support members 220, 222 are arranged on the nose contours. For example, a user can arrange the assembly 200B transversely along the contours of the nose and/or laterally along the contours of the nose to adjust for comfort. In some implementations, the user can arrange the assembly 200B transversely along the contours of the nose and/or laterally along the contours of the nose to adjust for heating or cooling particular portions of the nose to particular temperatures.

Similar to the nasal assembly 200A, the nasal assembly 200B includes a heat source (e.g., heat source 802 of FIG. 8) which may heat or cool a surface of the nose as described in detail herein. In addition, the nasal assembly 200B may include one or more sensors, power sources, and/or processors, as described in detail in FIG. 8.

Figure 2C:
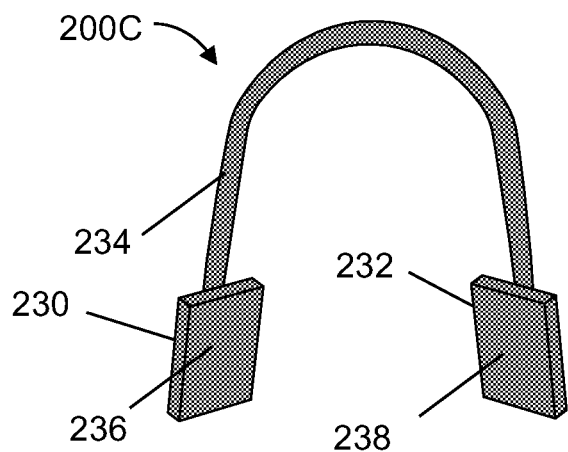
Figure 2D:
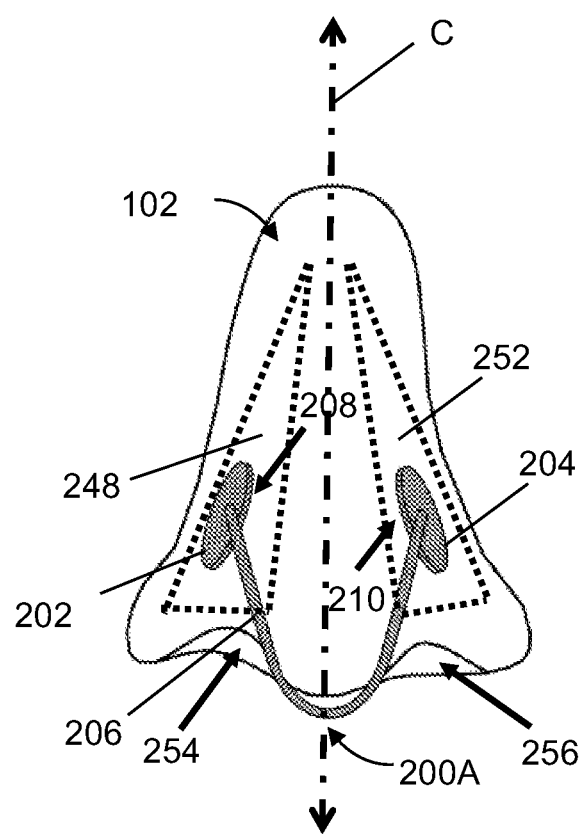

FIG. 2C illustrates a perspective view of yet another example nasal assembly 200C for warming at least a portion of the nasal cavity 104. The nasal assembly 200C may be a nose clip or nose adornment that may be removably coupled to be worn on the nose 102 of a user. The nasal assembly 200C includes a first support member 230 and a second support member 232. In some implementations, the first support member 230 is coupled to the second support member 232 by a bridge member 234, similar to bridge member 224 described above.

The first support member 230 includes a first surface 236 that is configured to substantially follow (and/or conform to and/or be in contact with) a sinistral contour 248 of the nose 102 when the nasal assembly 200C is being worn by a user. Similarly, the second support member 232 includes a second surface 238 that is configured to substantially follow (and/or conform to and/or be in contact with) the dextral contour 252 of the nose 102 when the nasal assembly 200B is being worn by a user.

As shown, the support members 230, 232 can be substantially square in shape. The square-shaped support members 230, 232 may be arranged along the contours of the nose to cover a portion of a surface area of the nose. While support members 230, 232 are depicted as square-shaped, one skilled in the art can contemplate substituting a different polygonal shape. The size of the portion of surface area may vary, as described throughout this disclosure. In addition, the support members 230, 232 may cover different portions of the surface area of the nose depending on how the support members 230, 232 are arranged on the nose contours. For example, a user can arrange the assembly 200C transversely along the contours of the nose and/or laterally along the contours of the nose to adjust for comfort. In some implementations, the user can arrange the assembly 200C transversely along the contours of the nose and/or laterally along the contours of the nose to adjust for heating or cooling particular portions of the nose to particular temperatures.

Similar to the nasal assembly 200A and nasal assembly 200B, the nasal assembly 200C includes a heat source (e.g., heat source 802 of FIG. 8) which may heat or cool a surface of the nose as described in detail herein. In addition, the nasal assembly 200C may include one or more sensors, power sources, and/or processors, as described in detail in FIG. 8. In general, the nasal assembly 200C may function in a similar fashion to nasal assemblies 200A and 200B and may execute the processes described herein.

FIG. 2D illustrates a side view of the nasal assembly 200A of FIG. 2A positioned on the nose 102 of a user. The nasal assembly 200A may be a nose clip or nose adornment that may be removably coupled to be worn on the nose 102 of a user. The nasal assembly 200A includes a first support member 202 and a second support member 204. In some implementations, the first support member 202 is coupled to the second support member 204 by the bridge member 206, as described above.

The first support member 202 includes a first surface 208 that is configured to substantially conform to a sinistral contour 248 of the nose 102 when the nasal assembly 200A is being worn by a user. Similarly, the second support member 204 includes a second surface 210 that is configured to follow a dextral contour 252 of the nose 102 when the nasal assembly 200A is being worn by a user.

In some implementations, the nasal assembly 200A may be positioned within the nose. For example, rather than positioning the assembly 200A on the external contours 248, 252, the support member 202 may be placed within nostril 254 while support member 204 is placed within nostril 256. The bridge member 206 may include or be composed of a shape memory alloy such as Nitinol® or a combination of one or more of: zinc, copper, iron, or gold. The bridge member 206 may function to press the support members 202, 204 against an interior surface within each nostril 254, 256.

Figure 2E:
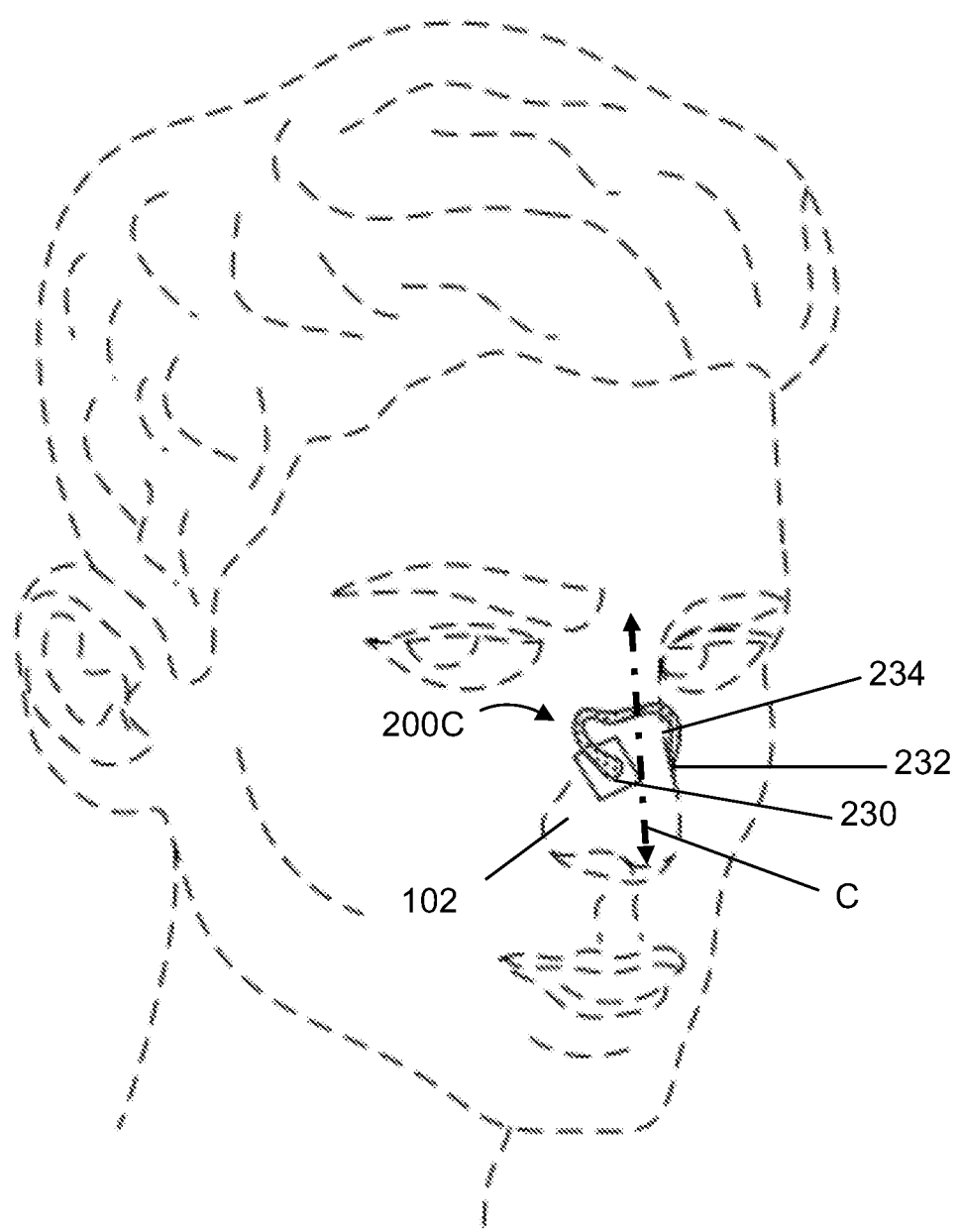

FIG. 2E illustrates a perspective view of the nasal assembly 200C of FIG. 2C on the nose 102 of the user. Here, the bridge member 234 may be under tension and apply pressure to the nose 102 through the support members 230, 232. For example, the bridge member 234 may be under tension to compress portions of the nose that are in contact with the support members 230, 232, which may cause an exerted pressure on the sinistral contour (e.g., sinistral contour 248 of FIG. 2D) of the nose, which may cause a sinistral wall (e.g., internal to the nose) to move inward toward a central axis (C) of the nose to narrow a sinistral nostril (e.g., nostril 254 of FIG. 2D). In addition, the compression may substantially simultaneously cause an exerted pressure on the dextral contour (e.g., dextral contour 252 of FIG. 2D) of the nose, which may cause a dextral wall (e.g., internal to the nose) to move inward toward the central axis (C) of the nose to narrow a dextral nostril (nostril 256 of FIG. 2D).

The nasal assembly 200C may further include a heat source (e.g., heat source 802 of FIG. 8) electrically coupled to the first support member 230 and the second support member 232. The heat source may be a wire, a coil, or other heating element arranged within the bridge member 234. The heat source may be electrically coupled to electronics and a power source of the nasal assembly 200C to heat or cool the surface of the nose. For example, the heat source may be powered and wired (as shown in FIG. 8) to adjust a surface temperature of portions of the nose in contact with support member 230 and support member 232.

In operation, the nasal assembly 200C may begin warming (or receive commands to warm) a portion of the nose 102 that is in contact with support members 230, 232. Warming a portion of the nose 102 may further cause warming of one or more internal portions of the nose 102 located within the nose and opposite the external anatomical regions of the nose. For example, the external anatomical regions of the nose may include a surface of at least one of: a bridge, a sinistral nasal sidewall, a dextral nasal sidewall, an accessory nasal cartilage, or a septal cartilage, as shown in FIG. 1. The assembly 200C may warm the portions of the nose 102 until a predefined external nose temperature or a predefined internal nose temperature is reached, as described in detail herein.

In some implementations, the bridge member 234 may include or be coupled to an antenna circuit 808 (FIG. 8) configured to wirelessly communicate with at least one external computing device 801 (FIG. 8) to enable the computing device 801 to wirelessly operate the nasal assembly 200C, as described in detail in FIG. 8. Such a circuit may enable wireless monitoring using sensors 804 to monitor and/or change a temperature of the nasal assembly 200C, an internal temperature of the nose, an external temperature of the nose, and/or an environmental temperature of an area surrounding the nasal assembly.

Figure 3A:
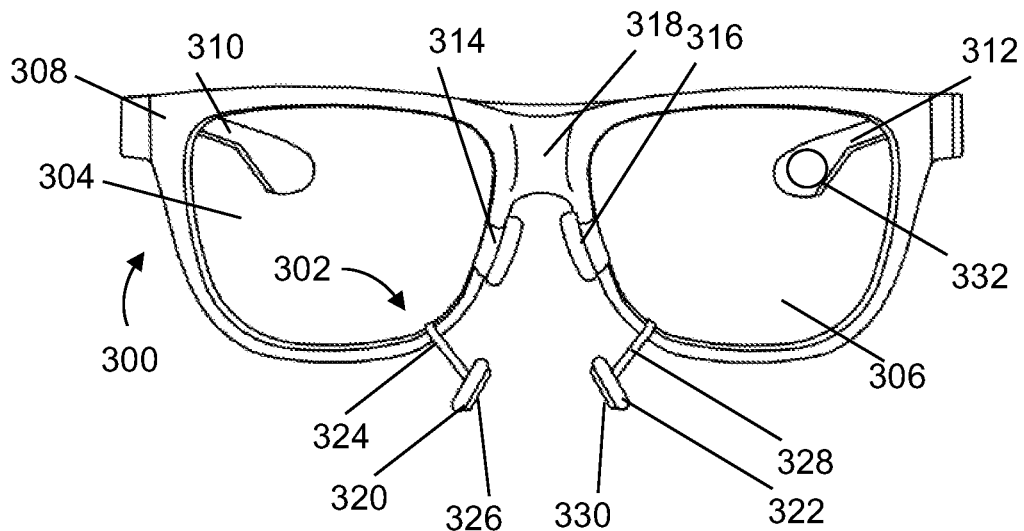
FIGS. 3A-3C illustrate an example embodiment of a nasal assembly that is part of a pair of eyeglasses.
Figure 3B:
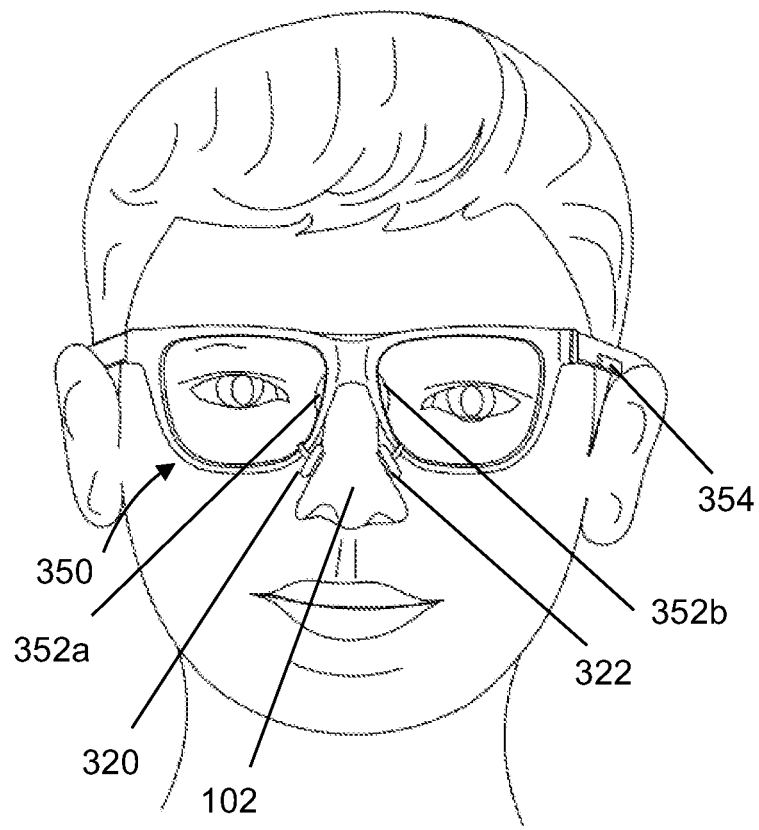
Figure 3C:
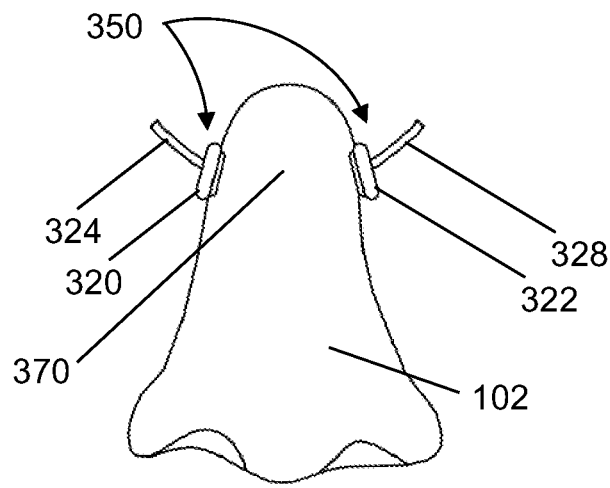

FIGS. 3A-3C illustrate an example embodiment of a nasal assembly 302 that is part of a pair of eyeglasses. FIG. 3A depicts eyeglasses 300 that include a nasal assembly 302. Similar to the nasal assemblies described in FIGS. 2A-2E, the nasal assembly 302 may function to heat a portion of a nose to reduce virus replication and/or to improve the efficiency of EV functioning in nasal mucosa.

The eyeglasses 300 may represent any one or more of reading glasses, augmented reality (AR) glasses, virtual reality (VR) glasses, head mounted display (HMD), or other head-based device. The eyeglasses 300 include lenses 304, 306 that are at least partially surrounded by frame 308 (e.g., rims). The frame 308 is coupled to temples 310, 312 (e.g., arms) and coupled to nose pads 314, 316. The frame 308 includes a bridge 318. In some implementations, the bridge 318 is connected to a first rim (not shown) and a second rim (not shown) when the frame 308 does not substantially surround the lenses 304, 306 (e.g., in wire rimmed glasses). The eyeglasses 300 may include hinges, screws (or other fasteners) to couple the frame 308 to the temples 310, 312 and/or to couple nose pads 314, 316 to the bridge 318 and/or frame 308.

The nasal assembly 302 can include a first support member 320 and a second support member 322. The first support member 320 is coupled to a distal end of a connecting member 324. The proximal end of the connecting member 324 is coupled to the frame 308 (or lens 304). The support member 320 includes a surface 326 that can substantially conform to a sinistral contour of a nose 102 when the nasal assembly 302 is being worn by a user.

The second support member 322 is coupled to a distal end of a connecting member 328. The proximal end of the connecting member 328 is coupled to the frame 308 (or lens 306). The support member 322 includes a surface 330 configured to substantially conform to a sinistral contour of a nose 102 when the nasal assembly 302 is being worn by a user.

The nasal assembly 302 also includes a heat source (e.g., heat source 802 of FIG. 8) that is electrically coupled to the first support member 320 and the second support member 322. The heat source 802 may be configured to adjust a surface temperature of the surface 326 and the surface 330 to cause warming of the sinistral contour of the nose and the dextral contour of the nose. The adjustment may include changing the temperature of the surfaces 326, 330 to change the temperature of the skin of the nose (and therefore a temperature within the nose) to bring the skin of the nose (e.g., nasal vestibule, bridge, septal cartilage, nasal sidewalls, etc.) to a predefined temperature range (e.g., about 41 degrees Celsius to about 43 degrees Celsius) and/or to bring an internal portion of the nose (e.g., nasal cavity, nasal mucosa, or inferior turbinate, etc.) to a predefined temperature range (e.g., about 37 degrees Celsius to about 39degrees Celsius).

In some implementations, the support member 320 coupled to connecting member 324 may be an extension of the eyeglass lens 304. Similarly, the support member 322 coupled to connecting member 328 may be an extension of eyeglass lens 306. For example, the proximal ends of respective connecting members 324, 328 may be coupled to respective portions of lenses 304, 306 to extend onto the nose of the user. In some implementations, the connecting members 324, 328 may function to compress an upper portion of the nose to provide an increase in restricted airflow. The restricted airflow may function to maintain a particular temperature of the nose to ensure that assembly 302 is efficient at heating and/or temperature maintenance of the nose.

In some implementations, the nasal assembly 302 also includes a battery charger 332. The battery charger 332 may be electrically coupled to one or more rechargeable batteries that may generate substantially continuous heating potential for assembly 302. As shown, the battery charger 332 is positioned on a temple 312 where a wall attachment can be connected. In such an example, the battery charger 332 can couple to the heat source 802 and/or any coupled memory, processor, sensors, etc. wired within frame 308, connecting member 328, connecting member 324, bridge 318, and/or temple 312.

FIG. 3B illustrates an example nasal assembly 350 on the nose 102 of a user. In this example, the nasal assembly 350 includes the support members 320, 322 on eyeglasses 300. The assembly 350 further includes a compression bridge 352a, 352b. The compression bridge 352a, 352b may function to compress an upper portion of the nose on both the sinistral and dextral sides to provide an increase in restricted airflow. The restricted airflow may function to maintain a particular temperature of the nose to ensure that assembly 350 is efficient at heating and temperature maintenance of the nose.

The assembly 350 can also include a sensor 354 installed on the temple 312. The sensor 354 may be an environmental sensor for sensing a temperature of an environment surrounding the assembly 350 (e.g., an ambient temperature). The assembly 350 may be operated based on measurements obtained by sensor 354. In some implementations, the sensor 354 may represent sensor 804. In some implementations, the sensor 354 may be added to assembly 350 in addition to sensor 804. In some implementations, sensor 354 may replace sensor 804 in assembly 350. One skilled in the art will appreciate that additional sensors may be contemplated for inclusion on assembly 350.

FIG. 3C illustrates the example assembly 350 that may be attached to eyeglasses/lenses and replacing nose pads on the eyeglasses. Providing heat along sinistral and dextral sides of the bridge 370 of the nose 102 can cause warming of the bridge and midline of the nose to warm the nasal cavity and/or nasal mucosa. In some implementations, the assembly 350 may also compress portions of the bridge of the nose to narrow air passageways within the nose, which may further increase a temperature of the nasal cavity.

In some implementations, the example assembly 350 may be removably applied to the nose via adhesive, for example. The support members 320, 322 may be applied along the nose 102 on one or more sides of the nose. Because the assembly 350 may be worn without additional supports and/or components, any number of support members 320, 322 may be applied to the nose to increase warming along the nose and/or to counteract an exceedingly cold environment external to the assembly 350.

Figure 4:
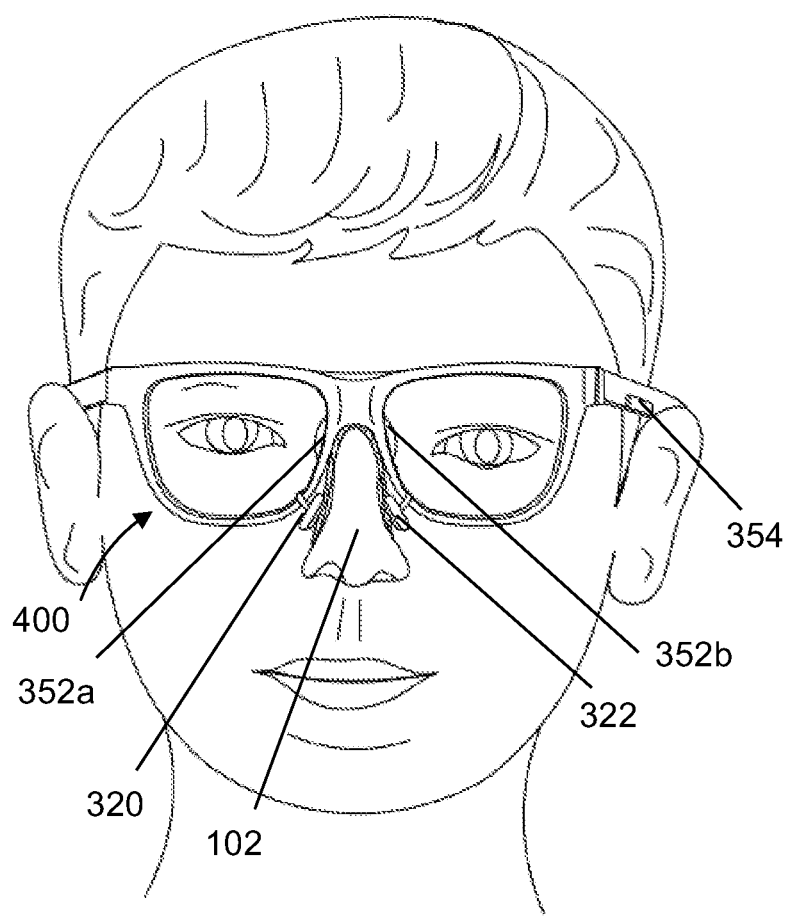
FIG. 4 illustrates another example embodiment of a nasal assembly that is part of a pair of eyeglasses.

FIG. 4 illustrates another example embodiment of a nasal assembly 350. The nasal assembly 350 includes the support members 320, 322, compression bridge 352a, 352b, and environmental sensor 354, as described in FIG. 3B. In this example, the compression bridge 352a, 352b may function to compress an upper portion of the nose on both the sinistral and dextral sides to restrict airflow. The restricted airflow may allow the nose to maintain a particular temperature to ensure that assembly 350 is efficient at heating and/or temperature maintenance of the nose.

In addition, the compression bridge 352a, 352b may also further warm the bridge of the nose. Thus, support members 320, 322 and bridge 352a, 352 may each warm a portion of the nose. Because additional warming components are provided in assembly 350, each component (e.g., members 320, 322, bridge 352a, 352b) may warm simultaneously to reduce an elapsed warming time to reach the predefined temperature range described herein. In some implementations, each component (e.g., members 320, 322, bridge 352a, 352b) may warm serially to reduce battery usage and/or energy usage of the assembly 350. Such sequencing of warming can be determined by artificial intelligence algorithms and/or machine learning models to optimize the warming effect and battery life. Providing warming and compression by the nasal assembly 350 can function to increase an internal temperature of the nose and synergistically warm the interior of the nose through congestion-based warming and external warming.

FIGS. 5A-5E illustrate example embodiments of internal nasal assemblies. The embodiments of FIGS. 5A-5E may be configured to apply warmth to internal portions of the nose 102 to trigger heating cycles that increase a temperature within the nasal cavity 104 and/or increase a temperature within one or more layers of the nasal mucosa including, but not limited to: the epithelium, the basement membrane, and the lamina propria and the cells, particles, and/or vesicles therein. When the one or more layers of the nasal mucosa are warmed to (or maintained at) a predefined temperature by the embodiments of FIGS. 5A-5E, extracellular vesicles (EVs) may increase within the nose, which may cause a reduction in the proliferation of viral cells in the nasal cavity. When the assemblies described herein are positioned in the nostril, air may be received through a hollow defined by the respective assembly.

In some implementations, the nasal assemblies shown in FIGS. 5A-5E may be flexible, bendable, compressible, or otherwise pliable to conform to a nostril. In some implementations, two nasal assemblies of a particular embodiment in FIGS. 5A-5E may be utilized in practice with a first nasal assembly in a first nostril and a second nasal assembly in a second nostril. While the two nasal assemblies are typically of the same embodiment type, one skilled in the art will recognize that the embodiments can be mixed and matched to utilize two different embodiment types in which a user may insert into their nostrils.

The nasal assemblies of FIGS. 5A-5E may be warmed externally before being inserted into a nostril. For example, the nasal assemblies may be warmed in heated water, a microwave, an oven, or the like. In some implementations, the nasal assemblies may encapsulate a variety of materials that may be heat activated upon agitating the materials and that can maintain heat for one to four hours, for example. Example materials may include iron powder, salt, activated carbon, and/or vermiculite.

In some implementations, the nasal assemblies of FIGS. 5A-5E may include electronics such as power sources, sensors, antennas, and/or processors, as described in detail herein. In such examples, the nasal assemblies of FIGS. 5A-5E may use such electronics to heat the assemblies, monitor the assemblies and/or environment surrounding the assemblies, and/or provide data associated with the heating of the assemblies or other operation of the assemblies.

When the heated nasal assemblies are inserted into the nostril, heat transfer from the assemblies to tissues and/or cavities within the nose can be achieved and may trigger an increase or maintenance of EVs within the nasal cavity while the assemblies remain above the predefined temperatures described herein and/or for a time after removal of the assemblies. In addition, the nasal assemblies may further function to provide a level of congestion that encourages heat retainment and generation, which may increase an internal temperature of a nostril, nasal cavity, etc.

In some implementations, the intranasal inserts of the embodiments of FIGS. 5A-5E may be additively manufactured, continuous lattice structures configured to generate a pressure on a surface of a portion of the nasal cavity when inserted into the nostril to cause a partial constriction of the nostril. For example, the intranasal inserts and/or the support structures described herein may be 3D printed components (e.g., intranasal nose inserts, nose pads, etc.) that have a lattice structure that may optimize for airflow through the nose with enough resistance to generate heat. By being 3D printed, these components can be custom-shaped to fit comfortably in the unique shape of a nostril of a user.

In some implementations, any one or more of the intranasal inserts of the embodiments of FIGS. 5A-5E may function or be used with any one of the external devices described in the embodiments of FIGS. 2A-4. For example, the bridge elements 252a, 252b of FIG. 4 may monitor an external skin surface of the nose 102. In such an example, the bridge elements 352a, 352b may not warm the nose, but may instead work in combination with internal assembly 500, for example, which may warm the interior surface of a nostril or nose cavity. The bridge elements 352a, 352b can work together to achieve a target temperature within a predefined temperature range, as described herein.

Figure 5A:
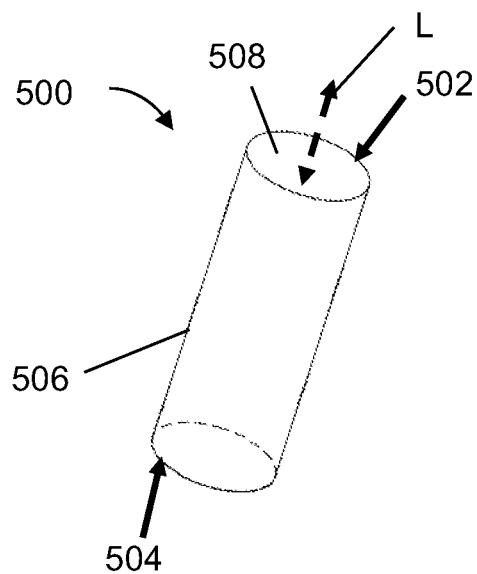
FIGS. 5A-5E illustrate example embodiments of internal nasal assemblies.

FIG. 5A illustrates an example nasal assembly 500 for use in a nose of a user. The nasal assembly 500 is shown as a substantially cylindrical, elongated, and substantially hollow body (e.g., tube, plug, intranasal insert, etc.) configured to be positioned at least partially within a nostril. The nasal assembly 500 may have a length sufficient to extend through a nasal vestibule of the nose and into at least a portion of the nasal cavity.

The nasal assembly 500 includes a proximal end 502 and a distal end 504, and a longitudinal axis (L) extending therethrough. The proximal end 502 may correspond to a portion of the assembly 500 that is furthest from the opening of the nostril when the assembly 500 is seated within the nostril. The nasal assembly 500 includes an exterior surface 506 that may be placed in contact with a portion of the nostril and nasal cavity. The nasal assembly 500 includes an interior surface 508 defining a hollow region to enable air to flow into the nostril, through the assembly 500, and into the nasal cavity and lungs.

Figure 5B:
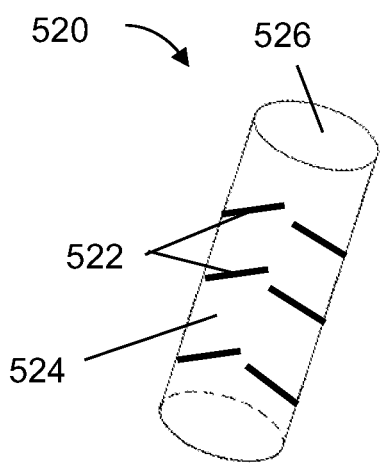

FIG. 5B illustrates an example nasal assembly 520 with one or more or a plurality of baffles (e.g., baffles 522). Similar to nasal assembly 500, nasal assembly 520 may be a substantially cylindrical and elongated body (e.g., tube, plug, intranasal insert, etc.) that is substantially hollow configured to be positioned at least partially within a nostril. The nasal assembly 520 may have a length sufficient to extend through a nasal vestibule of the nose and into at least a portion of the nasal cavity. The nasal assembly 520 includes an exterior surface 524 that may be placed in contact with a portion of the nostril and nasal cavity. The nasal assembly 520 includes an interior surface 526 defining a hollow region to enable air to flow into the nostril, through the assembly 500, and into the nasal cavity and lungs.

The baffles 522 are provided along the exterior surface 524 of the assembly 520 and may be defined through the exterior surface 524 as an opening into the hollow and interior surface 526 of the nasal assembly 520. In some implementations, the baffles 522 are stationary perforations in the assembly 520. In some implementations, the baffles 522 are nonstationary. The baffles 522 may be formed as flexible flaps, slits, cutouts, or perforations that allow air to flow from the interior surface 526 of the assembly 520 to the exterior surface 524 of the assembly 520. The baffles may provide at least two functions one is to provide restriction of the air flow into the nose to generate heat. Additionally, in situations where the nasal assembly is heated prior to insertion into the nostrils, the baffles can act as heat exchangers and transfer their heat to the passing air into the nose, which can raise the temperature of the internal tissues of the nose, thus reducing viral replication and increasing the EV response. The baffle design with flexible flaps, cutouts, slits, and perforations may be optimized to restrict airflow while still allowing effective breathing through the nose and while also maximizing a predefined level and/or exchange of heat to the passing air as the pre-heated baffle material is cooling.

Figure 5C:
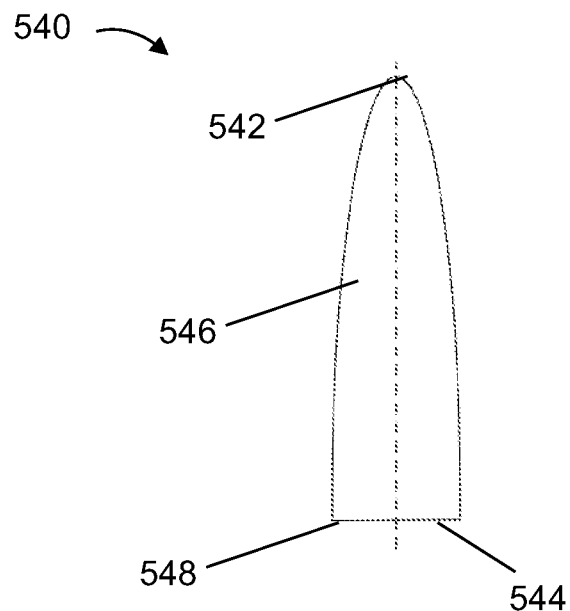

FIG. 5C illustrates another example nasal assembly 540 for use in a nose of a user. The nasal assembly 540 is depicted as a substantially elongated rounded cone-shaped or bullet-shaped body (e.g., plug, intranasal insert, etc.) that is substantially hollow therethrough and configured to be positioned at least partially within a nostril. An aperture (not shown) may be positioned at a proximal end 542 and may be defined from the proximal end 542 through to a distal end 544 of the assembly 540.

The nasal assembly 540 may have a length sufficient to extend through a nasal vestibule of the nose and into at least a portion of the nasal cavity. The nasal assembly 540 includes an exterior surface 546 that may be placed in contact with a portion of the nostril and nasal cavity. The nasal assembly 540 includes an interior surface (not shown) defining a hollow region to enable air to flow into the nostril, through the assembly 540, and into the nasal cavity and lungs.

The nasal assembly 540 may have a substantially circular base 548 at the distal end 544. The base 548 may have a substantially circular perimeter surrounding the hollow region defined by the aperture (not shown). In some implementations, the nasal assembly 540 may have an oval-shaped base 548 (or another shape) to accommodate varying nostril sizes.

While baffles are not shown on assembly 540, one skilled in the art could contemplate any combination of baffles being applied to assembly 540, as described herein.

Figure 5D:
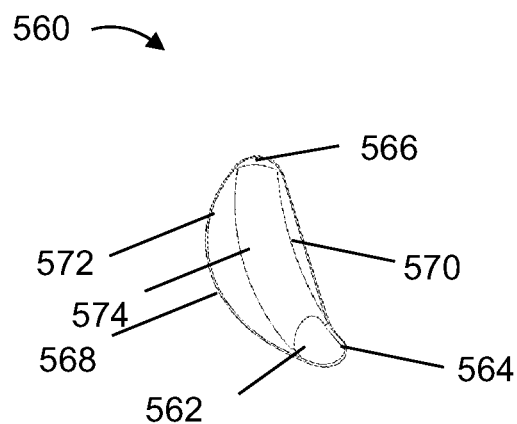
Figure 5E:
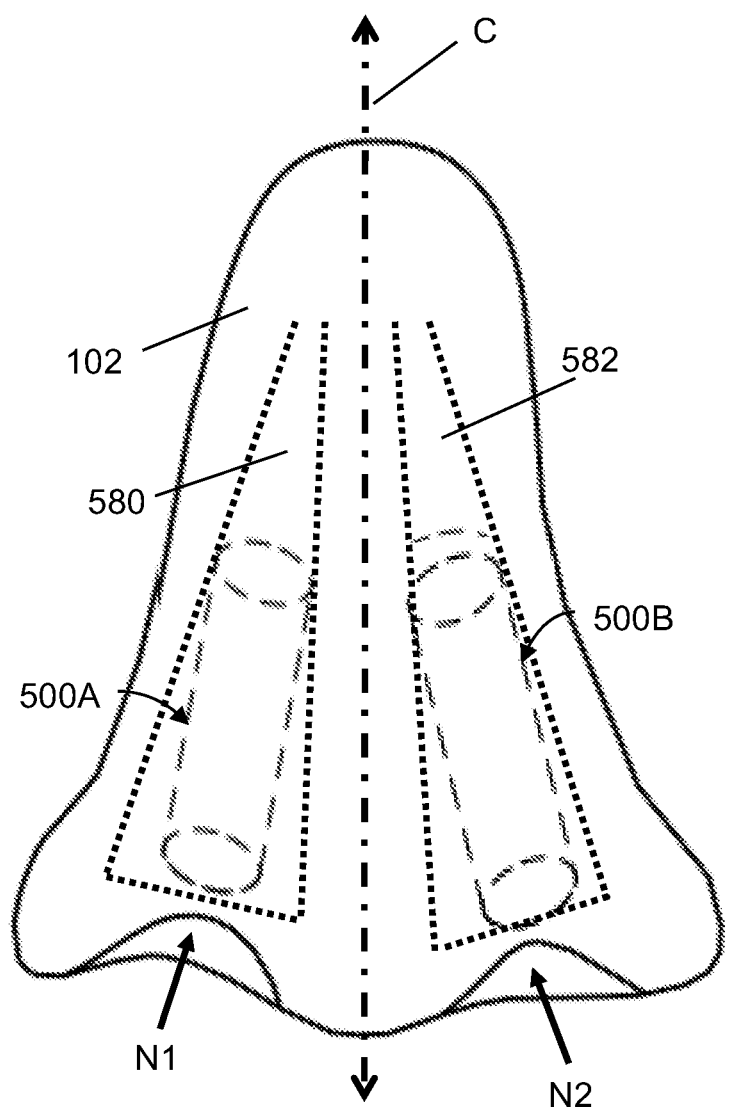

FIG. 5D illustrates yet another example nasal assembly for use in a nose of a user. The nasal assembly 560 is depicted as a substantially bulbous tube that is substantially hollow therethrough and positionable at least partially within a nostril. An aperture 562 may be positioned at a distal end 564 and may be defined from the distal end 564 through to a proximal end 566 of the assembly 560.

The nasal assembly 560 may be shaped as a general pear shape or garlic clove shape with a bulbous center portion 568 and a concave center portion 570 opposite the center portion 568. The nasal assembly 560 may have a length sufficient to extend through a nasal vestibule of the nose and into at least a portion of the nasal cavity. The nasal assembly 560 includes an exterior surface 572 that may be placed in contact with a portion of the nostril and/or nasal cavity. The nasal assembly 560 includes an interior surface (within tube 574) defining a hollow region to enable air to flow into the nostril, through the assembly 560, and into the nasal cavity and lungs. While baffles are not shown on assembly 560, one skilled in the art could contemplate any combination of baffles being applied to assembly 560, as described herein.

FIG. 5E illustrates the nasal assembly 500 within the nose 102. A sinistral contour 580 of the nose 102 is shown. The sinistral contour 580 is depicted as a broken line indicating that the contour 580 is within (e.g., internal to) the sinistral nostril. The sinistral contour 580 is within a first portion (e.g., sinistral nostril N1) of a nasal cavity of the nose 102. Similarly, a dextral contour 582 of the nose 102 is shown. The dextral contour 582 is depicted as a broken line indicating that the contour 582 is within (e.g., internal to) the dextral nostril. The dextral contour 582 is within a second portion (e.g., dextral nostril N2) of a nasal cavity of the nose 102.

In this example, the exterior surface 524 (FIG. 5A) of the nasal assembly 500A may be configured to cause warming of sinistral nostril N1 having the sinistral contour 580, for example, when assembly 500A is preheated (or configured to be electronically heated). The sinistral nostril N1 may have tissue portions lined with at least one mucous layer. These tissue portions and/or at least one mucous layer may also be warmed by nasal assembly 500A. Similarly, the exterior surface 524 (FIG. 5A) of the nasal assembly 500B may be configured to cause warming of dextral nostril N2 having the dextral contour 582, for example, when assembly 500B is preheated (or electronically heated).

The heating/warming of the external surfaces of assemblies 500A, 500B (and subsequent heating of nostrils N1, N2 and/or the corresponding nasal cavity or cavities) may be executed until a predefined temperature range is reached. For example, the predefined temperature range may be between about 37 degrees Celsius (about 98.6 degrees Fahrenheit) and about 39 degrees Celsius (about 102.2 degrees Fahrenheit). In some implementations, the predefined temperature range may be varied, as described in detail throughout this disclosure. The sinistral nostril Ni may have tissue portions lined with at least one mucous layer. These tissue portions and/or at least one mucous layer may also be warmed by nasal assembly 500A when the assembly 500A is placed in contact with the sinistral contour 580. Similarly, the dextral nostril N2 may have tissue portions lined with at least one mucous layer. These tissue portions and/or at least one mucous layer may also be warmed by nasal assembly 500B when the assembly 500B is placed in contact with the dextral contour 582.

In some implementations, the nasal assembly 500A and/or the nasal assembly 500B may include a sensor (e.g., sensor 804) adapted to be in contact with at least a portion of a nasal cavity of the nose. For example, at least one sensor 804 may be mounted on a portion of assembly 500A (and/or 500B). The sensor 804 may monitor a portion of the nasal cavity. In some implementations, the sensor 804 may be powered by a power source (e.g., power source 814) mounted on the assembly 500A and/or the assembly 500B. In this example, the power source may be electrically coupled to an electronic heat source (e.g., heat source 802) and the sensor 804.

Figure 6A:
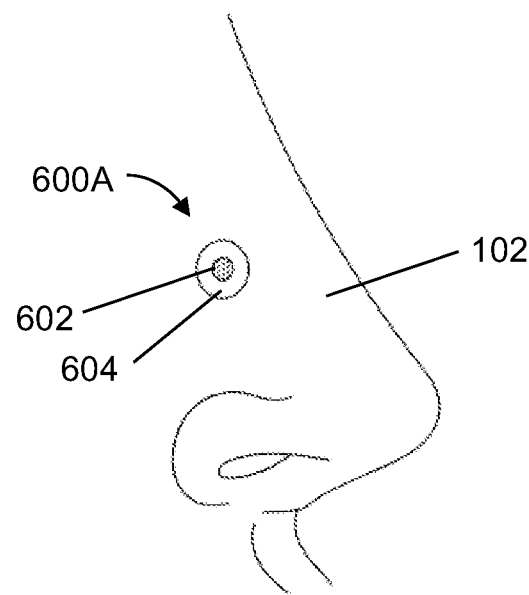
FIGS. 6A-6B illustrate an example embodiment of a nasal assembly for warming and/or monitoring a portion of the nose.
Figure 6B:
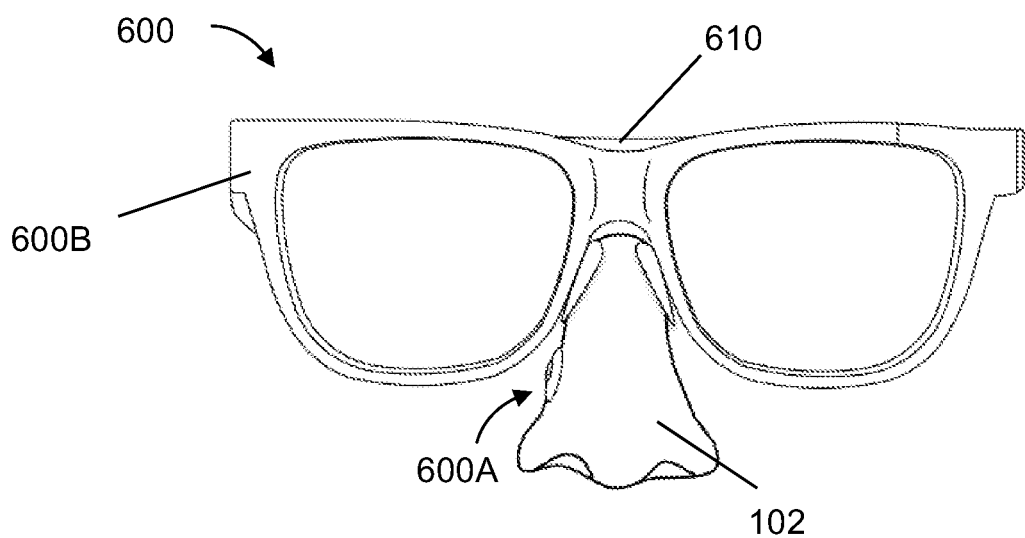

FIGS. 6A-6B illustrate an example embodiment of a nasal assembly 600 for warming and monitoring a portion of the nose. The nasal assembly may be two or more components that may function together to warm at least a portion of an interior nasal cavity 104 to inhibit viral replication within the nasal cavity.

FIG. 6A illustrates a jewelry component 600A that may be part of the nasal assembly 600 for warming and/or monitoring a portion of the nose such as the nasal cavity. The nasal assembly 600 may represent a wearable system for warming a nasal cavity. The wearable system may include at least one processor (e.g., processor 810), at least one sensor (e.g., sensor 804), and a heat source (e.g., heat source 802).

The jewelry component 600A includes a sensor 602 adapted to be placed adjacent to a portion of a nose. The sensor 804 may be installed in the jewelry component 600A which may be configured to be placed in a nose piercing associated with the nose such that the sensor 804 is in contact with the portion of the nasal cavity being monitored when the item of jewelry is worn in the nose piercing. The sensor 602 may be configured to sense a temperature of the portion of the nose and wirelessly output the sensed temperature to a processor (e.g., processor 810). In some implementations, the sensor 602 and/or processor 810 may use one or more antennas 604 (e.g., antenna circuitry 808) configured to wirelessly communicate with a mobile computing device (e.g., devices 101 and/or other computing device). The wireless communications may include temperature outputs, commands, and/or a status of the nasal assembly, status of the sensor, or the like.

While the jewelry component 600A shown here may be a nose piercing, one skilled in the art could contemplate that the component 600A may not be a piercing, but may instead be a magnetized two-part element with a first element in the nostril and a second element, magnetized to the first element when positioned over a skin site that is opposite a location of the first element in the nostril.

FIG. 6B illustrates an eyeglass component 600B of the nasal assembly 600 for warming and/or monitoring a portion of the nose. The eyeglass component 600B may be similar to eyeglasses 300 and nasal assembly 302. The component 600B includes a heat source 610 that may be communicatively coupled to the sensor 602 of component 600A and the processor (e.g., processor 810). As shown in FIG. 6B, the heat source 610 is placed in contact with a contour of the nose 102, such as the bridge of the nose. One skilled in the art could contemplate that the heat source 610 may be positioned in a different location on the nose, as discussed in detail herein. In addition, one skilled in the art could contemplate that the heat source 610 may alternatively be positioned on the jewelry component 600A instead of the eyeglass component 600B. In such an example, the heat source 610 may be an item of jewelry configured to be placed in a nose piercing associated with the nose 102 such that the heat source 610 is in contact with a portion of a nasal cavity associated with the nose 102 when the item of jewelry (e.g., jewelry component 600A) is worn in the nose piercing. The heat source 610 configured as jewelry may be configured to warm an interior surface of the nose 102 (e.g., at least a portion of a nasal cavity) in response to a sensor (e.g., sensor 602) detecting that the temperature of the nose 102 is outside of a target temperature range (e.g., the predefined temperature ranges defined herein).

Further, one skilled in the art could contemplate that separate heat sources 610 may alternatively be positioned on both the jewelry component 600A and the eyeglass component 600B to selectively warm either or both of the internal or external surface of the nose 102 until a predefined (e.g., target) temperature or temperature range is reached.

The processor 810 in the example nasal assembly 600 may be part of component 600A or part of component 600B. In some implementations, each component 600A, 600B includes a distinct and separate processor 810. In such an example, the separate processors 810 may be communicatively coupled. The one or more processors 810 of nasal assembly 600 may be configured to receive a sensed temperature of the nose 102 (and/or nasal cavity) from sensor 602 and may cause the heat source 610 to modify a temperature of the nasal cavity based on the sensed temperature of the nose 102 (and/or nasal cavity). For example, the one or more processors 810 may selectively activate the heat source 610, for example, (associated with a component based on a detected temperature of an environment surrounding the wearable system).

Figure 7:
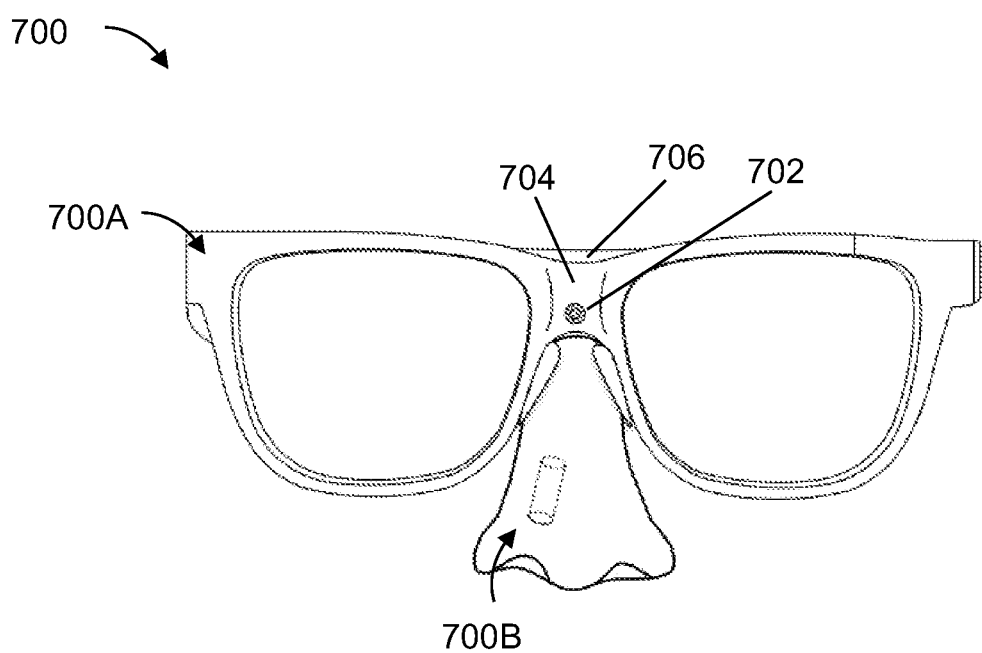
FIG. 7 illustrates an example embodiment of a nasal assembly for warming and/or monitoring a portion of the nose.

FIG. 7 illustrates an example embodiment of a nasal assembly 700 for warming and/or monitoring a portion of the nose. The nasal assembly 700 includes an eyeglass component 700A and an internal component 700B. The eyeglass component 700A may be similar to eyeglasses 300 and nasal assembly 302. In this example, the eyeglass component 700A may include a sensor 702. For example, the sensor 702 is shown here installed within a bridge member 704 of the eyeglass component 700A. In some implementations, the component 700B includes a sensor (not shown). In some implementations, both the eyeglass component 700A and the component 700B both include a sensor.

In some implementations, the eyeglass component 700A may also include a heat source 706 that may be communicatively coupled to the sensor 702 and one or more processors (e.g., processor 810). As shown in FIG. 7, the heat source 706 is placed in contact with a contour of the nose 102, such as the bridge of the nose. One skilled in the art could contemplate that the heat source 706 may be positioned in a different location on the nose, as discussed in detail herein. In addition, one skilled in the art could contemplate that the heat source 706 may alternatively be positioned on component 700B, for example, instead of the eyeglass component 700A. Further, one skilled in the art could contemplate that separate heat sources 706 may alternatively be positioned on both the component 700A and the component 700B to selectively warm either or both of the internal or external surface of the nose 102 until a predefined (e.g., target) temperature or temperature range is reached.

The processor 810 in the example nasal assembly 700 may be part of component 700A or part of component 700B. In some implementations, each component 700A, 700B includes a distinct and separate processor 810. In such an example, the separate processors 810 may be communicatively coupled. The one or more processors 810 of nasal assembly 700 may receive a sensed temperature of the nose 102 (and/or nasal cavity) from sensor 702 and may cause the heat source 706 to modify a temperature of the nasal cavity based on the sensed temperature of the nose 102 (and/or nasal cavity). For example, the one or more processors 810 may selectively activate the heat source 706.

In the example in which a sensor is included on the internal component 700B and adapted to be worn within a portion of the nasal cavity, the sensor 702 may monitor an internal temperature of the nasal cavity and wirelessly communicate with the processor and the heat source to trigger warming of the nasal cavity until a temperature within a target temperature range is achieved.

FIG. 8 is an example system 800 for warming and monitoring a portion of the nose. The system 800 may be a nasal assembly as described in FIGS. 2A-7 of this disclosure. The system 800 may be communicatively coupled to one or more mobile devices and/or computing devices 801. For example, the system 800 may provide temperature data, status data, message data, and/or other operational data to one or more devices 801. The one or more devices 801 may provide commands, instructions, and/or operational data to the system 800. In some implementations, the one or more devices 801 may provide data, commands, and/or status updates to system 800 via wireless communication, as described in detail herein.

As shown in FIG. 8, the system 800 includes a heat source 802. The heat source 802 may warm one or more components of system 800 to warm an interior or exterior surface of the nose. In some implementations, the heat source 802 may warm the nose using one or more radio frequency (RF) heating elements that may transmit energy from a nasal assembly (as described in FIGS. 2A-7) into or onto the nose. The one or more RF heating elements may function in a range of about 30 MHz to about 120 MHz.

In some implementations, the heat source 802 may warm the nose using one or more ultrasonic heating elements. The one or more ultrasound heating elements may function at a frequency of about 2 MHz to about 4 MHz. In some implementations, the frequency may be about 3 MHz.

In some implementations, the heat source 802 may warm the nose using one or more electromagnetic heating elements. The one or more electromagnetic heating elements may function at a frequency of about 902 MHz to about 928 MHZ.

In some implementations, the heat source 802 may warm the nose using a miniaturized Peltier warming device utilizing a thermoelectric device (TED). In some implementations, the heat source 802 may warm the nose using one or more infrared light emitting diodes. In some implementations, the heat source 802 may warm the nose using a solid state heat pump with thermally conductive graphene. In some implementations, the heat source 802 may warm the nose using one or more microelectromechanical (MEMS) micro-heat pumps. In some implementations, the heat source 802 may warm the nose using microwaveable clay or other materials that may be prewarmed and maintain heat for several hours. In some implementations, the heat source 802 may warm the nose using materials that are activated upon agitating the materials. Example materials may include iron powder, salt, activated carbon, and/or vermiculite.

The system 800 can include one or more sensors 804 (e.g., sensor 354, sensor 602, sensor 702,). The one or more sensors 804 may include a temperature sensor, a pressure sensor, a tissue impedance sensor, and/or an environmental temperature sensor. The temperature sensors may include, but are not limited to, infrared sensors, thermometers, thermistors, or thermal flux transducers. The one or more sensors 804 may be positioned on or within a bridge element, a support member, and/or other element associated with any of the nasal assembly devices described herein, such as system 800.

In some implementations, the one or more sensors 804 may be adapted to be worn within a portion of the nasal cavity. For example, the one or more sensors 804 may be positioned on one or more support members of a particular nasal assembly. When the one or more support members are inserted into the nasal cavity, the one or more sensors 804 may begin sensing and providing a status 820, for example, to devices 801. In some implementations, the one or more sensors 804 may be installed within a bridge member of a particular nasal assembly that may be worn on the nose.

The system 800 includes a communication module 806 to enable communications with one or more mobile or computing devices 801. The antenna circuitry 808 may enable system 800 to wirelessly communicate with one or more devices 801. For example, the communication module 806 may include antenna circuitry 808 (e.g., one or more antennas or coils) for wireless connections including, but not limited to Bluetooth, Wi-Fi, radio frequency (RF), or other near field communication protocol. In some implementations, the communication module 806 may also enable cellular data service for the system 800. The communication module 806 may also include components for wired connection, such as USB data transfer, or the like.

The system 800 can include one or more processors 810 coupled to memory 812 and power source 814. The one or more processors 810 may include one or more hardware processors, including microcontrollers, digital signal processors, application specific integrated circuit (ASIC), a field programmable gate array (FPGA) or other programmable logic devices, discrete gate or transistor logic, discrete hardware components, or any combination thereof designed to perform the functions described herein and/or capable of executing instructions, such as instructions stored by the memory 812. The processors 810 may also execute instructions for performing communications amongst the nasal assemblies described herein (e.g., system 800), sensors 804, and/or devices 801.

The memory 812 can include one or more non-transitory computer-readable storage media. The memory 812 may store instructions and data that are usable in combination with processors 810 to execute processes such as process 900. The memory 812 may also function to store or have access to sensor data, status 820 (e.g., status data), and commands 822.

The system 800 may further include (or be communicatively coupled to) input devices (not shown), output devices (not shown), and/or power source 814. The input devices may interact with one or more processors 810, memory 812, and/or sensors 804. The input devices may include buttons, touchscreens, switches, toggles, and/or other hardware components located on system 800. In some implementations, the input device may be external to or not integrated into the system 800 such that one or more controllers, mobile device (e.g., mobile device 801), etc., may communicate with system 800 using a wireless communications protocol.

The power source 814 may include or connect to a battery or a port for connecting system 800 to a power supply, an external battery, a wall power adapter, or the like.

In operation of system 800 (e.g., nasal assembly 200C), a heat source 802 may begin warming (or receive commands to warm) a portion of the nose 102 that is in contact with support members 230, 232. Warming a portion of the nose 102 may further cause warming of one or more internal portions of the nose 102 located within the nose and opposite the external anatomical regions of the nose. The assembly 200C may warm the portions of the nose 102 until a predefined external nose temperature or a predefined internal nose temperature is reached, as described in detail herein.

In addition, the nasal assembly 200C may include one or more sensors 804, power sources (e.g., power source 814), and/or processors (e.g., processors 810 (programmed to carry out monitoring instructions, communication instructions, and/or other device operation instructions). For example, the nasal assembly 200C may include one or more sensors 804 coupled to processors 810. The one or more sensors 804 may be adapted to be placed adjacent to or in contact with a portion of the nose 102. The one or more sensors 804 may be configured to sense a temperature of the portion of the nose 102 and wirelessly output the sensed temperature to the processor 810 via antenna circuitry 808.

In some implementations, the one or more sensors 804 may additionally or alternatively output a sensed temperature and/or status 820 to one or more devices 801. Devices 801 may provide commands 822 (e.g., command data) in response to the status 820 and/or in response to receiving a particular temperature from the sensors 804.

The one or more sensors 804 may include at least one temperature sensor for monitoring a temperature of an environment surrounding the nasal assembly 200C, for example, and transmit a signal to the heat source 802 to selectively activate the heat source 802 based on the temperature of the environment surrounding the nasal assembly 200C.

For example, the one or more devices 801 may monitor a temperature of the portion of the nasal cavity in preparation to generate commands that may trigger processes programmed into system 800 to warm (e.g., heat) portions of the nasal cavity. For example, the one or more devices 801 may receive from sensors 804 and/or processors 810, a surface temperature of a portion of the nasal cavity 104. In response to detecting that a surface temperature of the portion of the nasal cavity is below or outside of the predefined temperature range, as described herein, the one or more devices 801 may cause the heat source 802 to activate to perform a heating cycle.

In response to detecting that the surface temperature of the portion of the nasal cavity 104 is above the predefined temperature, as described herein, the one or more devices 801 may causing deactivation of the heat source 802. Monitoring can continue until the heating cycle is again triggered.

Example heating cycles may operate to warm a portion of the nose and/or a portion of the nasal cavity indefinitely until power loss is detected or for a programmed period of time that includes at least one of the following, but is not limited to the following: about 2 minutes to about 60 minutes; about 2 minutes to about 10 minutes; about 10 minutes to about 40 minutes; and about 40 minutes to about 60 minutes.

In some implementations, the heating cycles may operate to warm a portion of the nose and/or a portion of the nasal cavity for a percentage of each minute; a percentage of each hour or a percentage of each day. In some implementations, the heating cycles may operate to warm a portion of the nose and/or a portion of the nasal cavity based on a recipe indicating timed heating instructions/command based at least in part on which specific pathogen (e.g., viral, bacterial pathogen) is being operated upon to reduce replication. Such recipe could be determined using artificial intelligence algorithms and/or machine learning models.

In some implementations, a heating cycle may be executed according to a preprogrammed schedule. For example, the assemblies described herein may function automatically based on detection of a biological tissue and/or operate for the preprogrammed schedule upon application of a power source or on switch. In some implementations, a heating cycle may be executed according to a user-programmed period of time and user-programmed temperatures.

In some implementations, the heating cycles described herein may be automatically initiated in response to detecting available power to the heat source. In some implementations, the heating cycles described herein may be automatically initiated in response to detecting contact with skin or contact with nasal passage tissue. In some implementations, the heating cycles described herein may be automatically terminated in response to detecting a lack of contact with the skin or a lack of contact with nasal passage tissue. In some implementations, the heating cycles described herein may be performed according to a timed schedule based on an onboard clock or an onboard timer device. In some implementations, the heating cycles described herein may be performed according to user programming, user input, or other user-based request to operate a heating cycle with one or more of the assemblies described herein.

In some implementations, the bridge member 234 may include or be coupled to an antenna circuit 808 (FIG. 8) configured to wirelessly communicate with at least one external computing device 801 (FIG. 8) to enable the computing device 801 to wirelessly operate the nasal assembly 200C, as described in detail in FIG. 8. Such a circuit may enable wireless monitoring using sensors 804 to monitor and/or change a temperature of the nasal assembly 200C, an internal temperature of the nose, an external temperature of the nose, and/or an environmental temperature of an area surrounding the nasal assembly.

The embodiments of the devices/assemblies described herein may include nasal assemblies that are formed of a variety of materials. For example, the support structures and/or intranasal inserts described herein may be substantially formed of heat retaining materials that also provide biocompatibility and/or cleanability features. Such materials may include, but are not limited to Polyetheretherketone (PEEK), Nitinol® Styrene-Ethylene-Butylene-Styrene (SEBS), Silicone, Polycarbonate (PC), Polystyrene (PS), High-density polyethylene (HDPE), Low-density polyethylene (LDPE), Polyethylene (PE), Polypropylene (PP), Poly (methyl methacrylate) (PMMA), Polyethylene terephthalate glycol (PETG), Polyvinyl chloride (PVC), Acrylonitrile butadiene styrene (ABS), Nylon, Polyamide-imide (PAI), Polybenzimidazole (PBI), Polyimide (PI), Thermoplastic Polyurethane (TPU), and/or elastomer film polymers, foam, and/or combinations thereof.

In some implementations, the intranasal inserts and/or the support structures described herein are additively manufactured, continuous lattice structures configured to generate a pressure on a surface of a portion of the nasal cavity when inserted into the nostril to cause a partial constriction of the nostril. For example, the intranasal inserts and/or the support structures described herein may be 3D printed components (e.g., nose inserts, nose pads, etc.) that have a lattice structure that may optimize for airflow through the nose with enough resistance to generate heat. By being 3D printed, these components can be custom-shaped to fit comfortably in the unique shape of a nostril of a user.

The bridge members and/or jewelry may be formed of any one of the materials above and/or metals such as gold, silver, platinum, stainless steel, titanium, aluminum, nickel, Monel™, gemstones, diamond, or combinations thereof.

The support members of the devices described herein may include surface areas sized to cover any portion of the exterior of the nose. For example, the support members may have a width and length that may fit within a portion of the contour of an exterior surface of the nose. In some implementations, the support members described herein may have a width and length that may fit within a portion of the contour of an interior surface of the nose. For example, the support members described herein may be sized to have a width of about 12.7 millimeters to about 31.8 millimeters; about 12.7 millimeters to about 15 millimeters; about 15 millimeters to about 20 millimeters; about 20 millimeters to about 25 millimeters; about 25 millimeters to about 30 millimeters; or about 30 milometers to about 31.8 millimeters. In some implementations, the width may be sized by an end user before wearing the devices described herein. For example, the support members described herein may have a modifiable perimeter that may be cut, folded or otherwise modified to change a shape of the support member before a user adheres the support member surface to the nose.

Similarly, the support members described herein may be sized to have a length of about 12.7 millimeters to about 31.8 millimeters; about 12.7 millimeters to about 15 millimeters; about 15 millimeters to about 20 millimeters; about 20 millimeters to about 25 millimeters; about 25 millimeters to about 30 millimeters; or about 30 milometers to about 31.8 millimeters. In some implementations, the length may be sized by an end user before wearing the devices described herein. For example, the support members described herein may have a modifiable perimeter that may be cut, folded, or otherwise modified to change a shape of the support member before a user adheres the support member surface to the nose.

In some implementations, the length of the support members may differ from the width of the support members. For example, the length may be about 1.2 times the width; about 1.5 times the width; about 2.0 times the width, etc.

The support members described herein may be sized to have a depth of about 0.5 millimeters to about 5 millimeters; about 0.5 millimeters to about 1 millimeter; about 1 millimeter to about 1.5 millimeters; about 1.5 millimeters to about 2 millimeters; about 2 millimeters to about 2.5 millimeters; about 2.5 millimeters to about 3 millimeters ; about 3 millimeters to about 3.5 millimeters; about 3.5 millimeters to about 4 millimeters; about 4 millimeters to about 4.5 millimeters; or about 4.5 millimeters to about 5 millimeters. The support members described herein may be flexible members that conform to a portion of the nose. In some implementations, the support members may vary in depth across a surface of the support member to account for electronics, batteries, electronics, heat sources, and the like.

In some implementations, the devices described herein may be configured to be stored and powered in a case. For example, a battery source of the nose assemblies described herein may be adapted to be charged within a case designed to hold and protect the assemblies. The case may charge the assemblies in a wired or wireless fashion. In some implementations, the case may provide warming of a nasal assembly such that the nasal assembly may be unpowered, in general, but able to perform warming of the nasal cavity based on emitting heat from a prewarmed state.

Methods

Figure 9:
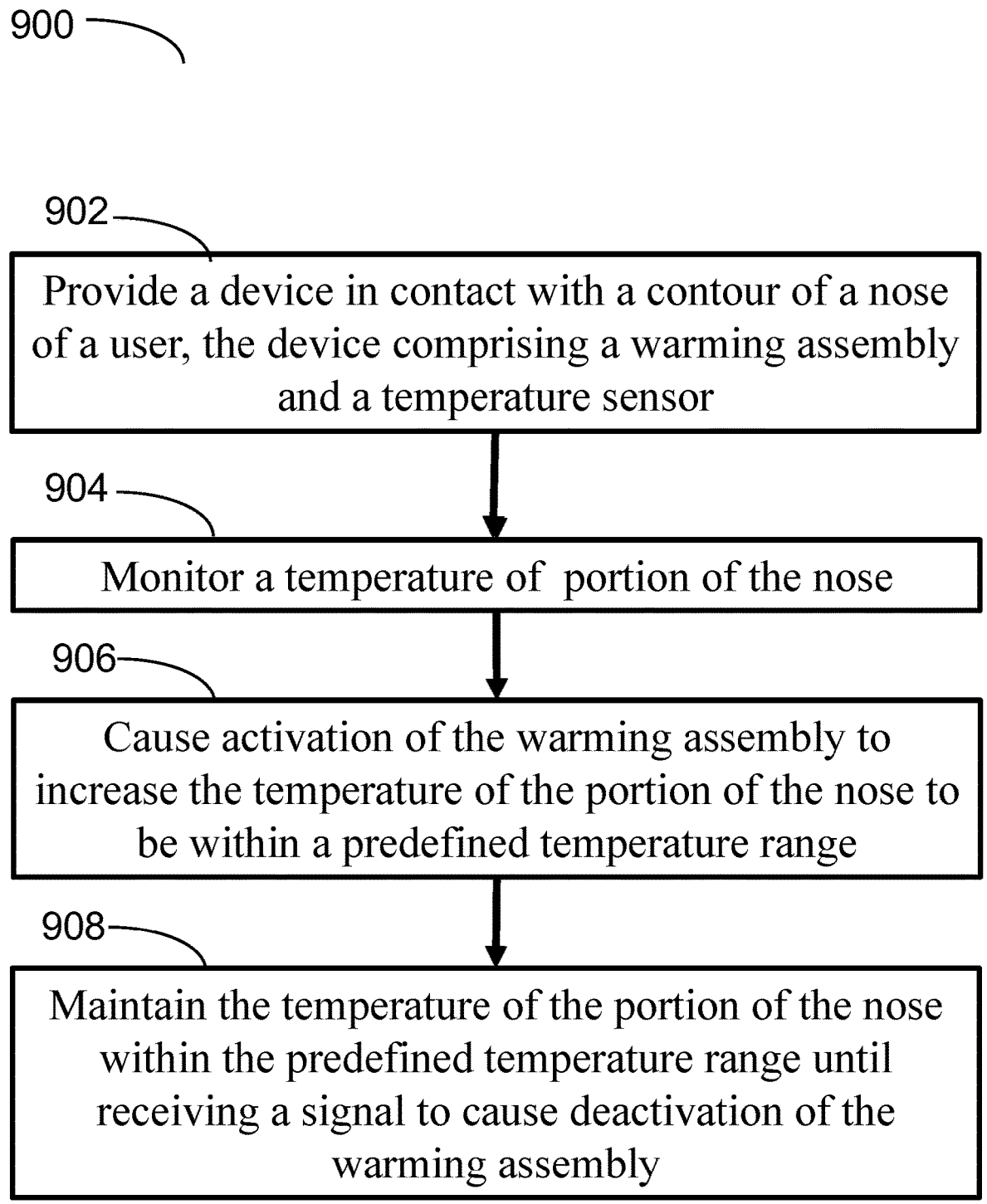
FIG. 9 is an example process for reducing virus replication or bacterial particle infection in a nasal mucosa.

As shown in FIG. 9, a process for reducing virus replication and/or enhancing EV effectiveness in a nasal mucosa may include monitoring, determining temperatures, and adjusting and/or maintaining temperatures associated with the nose. The process 900 functions to ensure that the nasal cavity and/or nasal mucosa of the nose is within a predefined temperature range to ensure reduction in virus and/or bacterial replication within the nose. The process 900 is generally used for reducing illness and severity of illness, but can additionally or alternatively be used for any suitable applications, clinical or otherwise. The process 900 can be configured and/or adapted to function for any suitable warming method for portions of the body. For example, the process 900 may be used for patient warming during surgery when operated with increased energy levels and/or temperatures to potentially increase a core body temperature, possibly prevent hospital acquired infections, and as such, process 900 may be used in conjunction with other conventional methods.

The process 900 may be used with any of the internal and external devices (e.g., nasal assemblies) described herein to increase the temperature of the interior of the nose (including the inferior turbinate). In some implementations, the devices described herein may be used to heat airways of patients for therapeutic purposes, for example, in clinical conditions where increasing the temperature of the airway is desirable. While assembly 200A and assembly 500 may be used as examples in the process described below, any one or more of the nasal assemblies described herein may be substituted.

At block 902, the process 900 includes providing a device in contact with a contour of a nose of a user. For example, the device (e.g., assembly) may include any one or more of assemblies 200A, 200B, 200C, 300, 350, 500, 520, 540, 560, 600 and/or 700. Each device utilized in process 900 may include a warming assembly (e.g., heat source 802) and a temperature sensor (e.g., sensor 804). Each device may at least partially constrict or restrict airflow into the nose. For example, at least partially constricting or restricting airflow into the nose may include at least partially obstructing a nostril of the nose. In some implementations, at least partially constricting or restricting airflow into the nose may include at least partially obstructing both a dextral nostril and a sinistral nostril. For example, when the device is an internal assembly (e.g., nasal assembly 500), the device may at least partially restrict or block a portion of the nostril in which the assembly resides. However, when the device is an external assembly (e.g., nasal assembly 200A), the device may apply pressure on one or both nostrils, a bridge of the nose, sides of the bridge of the nose, or one or more sidewalls of the nose to at least partially restrict or block an amount of air that enters the nostrils.

At block 904, the process 900 includes monitoring, by the temperature sensor 804, a temperature of portion of the nose. For example, the temperature sensor 804 may be electrically coupled to the nasal assembly 200A. The temperature sensor 804 may sense a temperature of the external sidewall of the nose under, in contact with, or proximal to a particular support member (e.g., support member 202, support member 204). In some implementations, the temperature sensor 804 may sense a temperature surrounding the nasal assembly 200A. In some implementations, the temperature sensor 804 may sense a temperature within the nasal cavity when, for example, assembly 500 is operating within a nostril.

The detected temperature(s) may trigger the nasal assembly 200A or the nasal assembly 500 to modify a temperature profile of a heat cycle. In some implementations, the detected temperature(s) may trigger the nasal assembly 200A or the nasal assembly 500 to modify a temperature (or temperature range) to reach. In some implementations, the detected temperature(s) may trigger the nasal assembly 200A or the nasal assembly 500 to modify other functionality of the assemblies 200A, 500.

At block 906, the process 900 includes detecting, by the temperature sensor, whether the temperature for a portion of the nose is below a predefined temperature range. For example, the sensor 804 may function in combination with processor 810 to detect whether the temperature of a portion of the nose drops below the predefined temperature range.

When the device is an internal assembly (e.g., nasal assembly 500), the portion of the nose may include an inferior turbinate (FIG. 1) and the predefined temperature range may be about 37 degrees Celsius (about 98.6 degrees Fahrenheit) to about 39 degrees Celsius (about 102.2 degrees Fahrenheit). When the device is an external assembly (e.g., nasal assembly 200A), the portion of the nose may include the nasal vestibule (FIG. 1) and the predefined temperature range may be about 41 degrees Celsius (about 105.8 degrees Fahrenheit) to about 43 degrees Celsius (about 109.4 degrees Fahrenheit).

In response to detecting that a temperature of the internal or external nose portion is below the predefined temperature range(s), the process 900 includes causing activation of the warming assembly (e.g., heat source 802) to increase the temperature of the portion of the nose to be within a predefined temperature range. In short, the detection of a temperature outside of the predefined temperature range may cause an automatic activation of the heat source associated with the assembly (coupled to the sensor 804) performing the temperature measurement.

In the event that the temperature of the internal or external nose portion is detected to be within the predefined temperature range, the process 900 may include deactivating the warming assembly (e.g., heat source 802). In addition, the process 900 may also deactivate the warming assembly (e.g., heat source 802) when the portion of the nose reaches a temperature within the predefined temperature range.

In some implementations, the assemblies described herein may include an antenna circuit (e.g., antenna circuit 808) that is configured to communicate wirelessly with at least one external computing device (e.g., one or more devices 801) to enable the at least one external computing device (e.g., one or more devices 801) to wirelessly operate the assembly. Temperature data, commands 822, statuses 820, or the like may be transmitted from the assemblies described herein to one or more external devices, such as devices 801.

At block 908, the process 900 includes maintaining the temperature of a portion of the nose to be within the predefined temperature range until receiving a signal to cause deactivation of the warming assembly. For example, the sensor 804 in combination with the processor 810 (e.g., programmed to carry out monitoring instructions, communication instructions, and/or other device operation instructions) may monitor a temperature of an environment surrounding a portion of the assembly 500, for example and may send a signal to the warming assembly (e.g., heat source 802) to selectively activate the warming assembly (e.g., heat source 802) based on the detected temperature of the environment surrounding the portion of the assembly 500. In some implementations, the processor 810 (e.g., programmed to carry out monitoring instructions, communication instructions, and/or other device operation instructions) may monitor a temperature of one or more nose portions and/or nasal cavity substantially adjacent to (e.g., near or in contact with) assembly 300 (or assembly 200A or assembly 500), for example, and may send a signal to the warming assembly (e.g., heat source 802) to selectively activate the warming assembly (e.g., heat source 802) based on the temperature detected for the one or more nose portions and/or nasal cavity substantially adjacent to assembly 300 (or assembly 200A or assembly 300).

The systems and methods described herein and variations thereof can be embodied and/or implemented at least in part as a machine configured to receive a computer-readable medium storing computer-readable instructions. The instructions may be executed by computer-executable components integrated with the system and one or more portions of the processor on the nasal assemblies described herein and/or computing devices 801. The computer-readable medium can be stored on any suitable computer-readable media such as RAMs, ROMs, flash memory, EEPROMs, optical devices (e.g., CD or DVD), hard drives, floppy drives, or any suitable device. The computer-executable component may include any suitable dedicated hardware or hardware/firmware combination that can alternatively or additionally execute the instructions.

References in the specification to "one embodiment," "an embodiment," "an illustrative embodiment," "some embodiments," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

As used in the description and claims, the singular form "a", "an" and "the" include both singular and plural references unless the context clearly dictates otherwise. For example, the term "sensor" may include, and is contemplated to include, a plurality of sensors. At times, the claims and disclosure may include terms such as "a plurality," "one or more," or "at least one;" however, the absence of such terms is not intended to mean, and should not be interpreted to mean, that a plurality is not conceived.

The term "about" or "approximately," when used before a numerical designation or range (e.g., to define a length or pressure), indicates approximations which may vary by (+) or (−) 5%, 1% or 0.1%. All numerical ranges provided herein are inclusive of the stated start and end numbers. The term "substantially" indicates mostly (i.e., greater than 50%) or essentially all of a device, substance, or composition.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a system or method consisting essentially of the elements as defined herein would not exclude other materials, features, or steps that do not materially affect the basic and novel characteristic(s) of the claimed disclosure. "Consisting of" shall mean that the devices, systems, and methods include the recited elements and exclude anything more than a trivial or inconsequential element or step. Embodiments defined by each of these transitional terms are within the scope of this disclosure.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the disclosed subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A nasal assembly comprising:

a first support member having a first surface configured to substantially conform to a sinistral contour of a nose when the nasal assembly is being worn;

a second support member having a second surface configured to follow a dextral contour of the nose when the nasal assembly is being worn; and a heat source electrically coupled to the first support member and the second support member, the heat source being configured to adjust a surface temperature of the first surface and the second surface to cause warming of the sinistral contour of the nose and the dextral contour of the nose to a predefined temperature range, wherein the first support member and the second support member are coupled to a compression bridge member configured to compress an upper portion of the nose to at least partially restrict a portion of airflow through passageways within the nose when the nasal assembly is being worn, wherein the warming and the compression cause a reduction in replication of viral cells in the nose.

2. The nasal assembly of claim 1, wherein the nasal assembly further comprises:

an antenna circuit configured to communicate wirelessly with at least one external computing device to enable the at least one external computing device to wirelessly operate the nasal assembly.

3. The nasal assembly of claim 1, wherein:

the sinistral contour of the nose and the dextral contour of the nose are external anatomical regions of the nose; and the first surface and the second surface are configured to cause warming of one or more internal portions of the nose to a second predefined temperature range when the first surface and the second surface are heated, wherein the one or more internal portions of the nose are opposite the external anatomical regions of the nose at respective locations of the sinistral contour and the dextral contour of the nose.

4. The nasal assembly of claim 3, wherein:

the external anatomical regions of the nose comprise a surface of at least one of: a bridge, a sinistral nasal sidewall, a dextral nasal sidewall, an accessory nasal cartilage, or a septal cartilage; and heating the first surface and the second surface causes warming of the one or more internal portions of the nose to the second predefined temperature range, the one or more internal portions of the nose being opposite the respective bridge, the sinistral nasal sidewall, the dextral nasal sidewall, the accessory nasal cartilage, or the septal cartilage.

5. The nasal assembly of claim 3, wherein:

the predefined temperature range is about 41 degrees Celsius to about 43 degrees Celsius; and the second predefined temperature range is about 37 degrees Celsius to about 39 degrees Celsius.

6. The nasal assembly of claim 1, wherein the first support member is coupled to the second support member by the compression bridge member, wherein the compression bridge member has a substantially C-shaped structure.

7. The nasal assembly of claim 1, wherein the nasal assembly is configured to removably attach to a lens of eyeglasses.

8. The nasal assembly of claim 1, wherein at least partially restricting a portion of airflow through passageways within the nose comprises at least partially constricting at least one nostril of the nose.

9. The nasal assembly of claim 1, wherein at least partially restricting a portion of airflow through passageways within the nose further enables the nasal assembly to efficiently maintain temperature of nasal mucosa in the nose.

10. The nasal assembly of claim 1, wherein the nasal assembly is a pair of eyeglasses, the nasal assembly further comprising:

a battery charger for generating continuous heating for the nasal assembly, the battery charger being:

electrically coupled to one or more rechargeable batteries and the heat source;

positioned on a temple portion of the pair of eyeglasses; and configured to receive a power attachment connection at the temple portion.

11. The nasal assembly of claim 1, wherein warming the sinistral contour of the nose and the dextral contour of the nose to the predefined temperature range comprises warming a vestibule of the nose.

12. The nasal assembly of claim 1, wherein warming the sinistral contour of the nose and the dextral contour of the nose to the predefined temperature range is performed according to a heating cycle selected based at least in part on an indicated pathogen.

13. The nasal assembly of claim 1, further comprising:

a second heat source coupled to the compression bridge member and configured to warm a bridge of the nose while the first heat source warms the sinistral contour and the dextral contour, wherein the compression bridge member comprises a first end and a second end, the first end being coupled to the first support member and the second end being coupled to the second support member.

14. The nasal assembly of claim 1, wherein the heat source is an ultrasonic heat source operating at a frequency range from about 2 MHz to about 4 MHz.

15. The nasal assembly of claim 1, wherein the warming of the sinistral contour of the nose and the dextral contour of the nose and the compression of the upper portion of the nose further causes an increase in extracellular vesicle generation in nasal mucosa of the nose.

16. The nasal assembly of claim 1, wherein the compression bridge member is formed of a shape memory material to enable flexible movement for applying force to the nose.

17. A wearable system for warming a nasal cavity, the system comprising:
   a processor;
   a sensor adapted to be placed adjacent to a portion of a nose and configured to sense a temperature of the portion of the nose and wirelessly output the sensed temperature to the processor; and
   a heat source communicatively coupled to the sensor and the processor, the heat source being placed in contact with a contour of the nose,
   wherein the heat source is coupled to a bridge member configured to compress the contour of the nose to at least partially restrict a portion of airflow through passageways within the nose when the wearable system is being worn,
   wherein the processor is configured to receive the sensed temperature of the nose and cause the heat source to modify a temperature of the nasal cavity based on the sensed temperature of the nose; and
   wherein the modifying of the temperature and the compression of the contour of the nose cause a reduction in replication of viral cells in the nose.

18. The system of claim 17, further comprising one or more antennas configured to wirelessly communicate with a mobile computing device to selectively activate the heat source based on a detected temperature of an environment surrounding the wearable system.

19. A method for reducing viral replication within a nasal cell, the method comprising:
   providing a wearable device comprising:
      a first support member having a first surface configured to substantially conform to a sinistral contour of a nose of a user;
      a second support member having a second surface configured to follow a dextral contour of the nose; and
      a temperature sensor coupled to a portion of the wearable device; and
      a heat source electrically coupled to the first support member and the second support member, the heat source being configured to adjust a surface temperature of the first surface and the second surface to cause warming of the sinistral contour of the nose and the dextral contour of the nose to a predefined temperature, wherein the first support member and the second support member are coupled to a compression bridge member configured to compress a portion of the nose to at least partially restrict a portion of airflow through passageways within the nose;
   monitoring, by the temperature sensor, a temperature of the portion of the nose;
   in response to detecting, by the temperature sensor and for the portion of the nose, that the temperature is below the predefined temperature, causing activation of the heat source to increase the temperature of the portion of the nose to be within a predefined temperature range; and
   maintaining the temperature of the portion of the nose within the predefined temperature range until receiving a signal to cause deactivation of the heat source.

20. The method of claim 19, wherein the warming of the sinistral contour of the nose and the dextral contour of the nose and the compression of the portion of the nose causes an increase in extracellular vesicle generation in nasal mucosa of the nose.

21. The method of claim 19, wherein the compression bridge member is formed of a shape memory material to enable flexible movement for applying force to the nose.

22. The method of claim 19, wherein at least partially restricting a portion of airflow through passageways within the nose comprises at least partially constricting at least one nostril of the nose.

23. The method of claim 19, wherein at least partially restricting a portion of airflow through passageways within the nose further enables the wearable device to efficiently maintain temperature of nasal mucosa in the nose.

24. The method of claim 19, wherein the wearable device is a pair of eyeglasses, the wearable device further comprising:
   a battery charger for generating continuous heating for the wearable device, the battery charger being:
      electrically coupled to one or more rechargeable batteries, the temperature sensor, and the heat source;
      positioned on a temple portion of the pair of eyeglasses; and
      configured to receive a power attachment connection at the temple portion.

25. The method of claim 19, wherein warming the sinistral contour of the nose and the dextral contour of the nose to the predefined temperature comprises warming a vestibule of the nose.

26. The method of claim 19, wherein warming the sinistral contour of the nose and the dextral contour of the nose to the predefined temperature is performed according to a heating cycle selected based at least in part on an indicated pathogen.

* * * * *